(12) United States Patent
Luk et al.

(10) Patent No.: US 7,960,338 B2
(45) Date of Patent: Jun. 14, 2011

(54) METHODS AND COMPOSITIONS FOR TREATMENT OF ENDOTOXIN-MEDIATED PRO-INFLAMMATORY RESPONSES

(75) Inventors: John Moon Ching Luk, Hong Kong (HK); Kwong Fai Wong, Hong Kong (HK); Ronnie Tung Ping Poon, Hong Kong (HK); Sheung Tat Fan, Hong Kong (HK)

(73) Assignee: The University of Hong Kong, Hong Kong (HK)

( * ) Notice: Subject to any disclaimer, the term of this patent is extended or adjusted under 35 U.S.C. 154(b) by 0 days.

(21) Appl. No.: 12/502,548

(22) Filed: Jul. 14, 2009

(65) Prior Publication Data

US 2010/0008925 A1    Jan. 14, 2010

Related U.S. Application Data

(60) Provisional application No. 61/080,558, filed on Jul. 14, 2008.

(51) Int. Cl.
*A01N 37/18*    (2006.01)
(52) U.S. Cl. .......... 514/2.1; 530/350; 530/399; 514/2.4; 514/9.4; 514/18.7; 424/234.1
(58) Field of Classification Search .................. None
See application file for complete search history.

(56) References Cited

U.S. PATENT DOCUMENTS

2004/0127416 A1* 7/2004 Massia et al. ................... 514/12

FOREIGN PATENT DOCUMENTS

| WO | WO 2004/045542 A2 * | 6/2004 |
| WO | WO 2004/066914 A2 * | 8/2004 |

OTHER PUBLICATIONS

Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Wong et al, Characterization of Two Novel LPS-Binding Sites in Leukocyte Integrin BA Domain, The FASEB Journal, Research Communication, vol. 27, Oct. 2007.
Wong et al, Integrin CD 18-BA Peptide is a Potent Endotoxin Antagonist in Murine Sepsis.
Wong et al, Experimental Therapeutics for Protection of Liver Failure from Endotoxin-Mediated Sepsis, Mar. 2008.
Strauss. Hybridization with radioactive Probes. Current Protocols in Molecular Biology, 1993.
Ho, et al. Galactosamine-induced Fulminant Liver Failure—Observation in a Porcine Model. Asian Journal of Surgery, Jan. 2002, pp. 73-79.
Hybridization of Southern Filters. Southern Transfer, Analysis of Recombinant DNA Clones, pp. 387-389.
Ohman, et al. Solvent stabilized solution structures of galanin and galanin analogs, studied by circular dichroism spectroscopy. Biochimica et Biophysica Acta 1236, 1995, pp. 259-265.
Wong, et al. Characterization of two novel LPS-binding sites in leukocyte integrin BA domain. The FASEB Journal, Oct. 2007. pp. 3231-3239.

* cited by examiner

*Primary Examiner* — Jennifer E Graser
(74) *Attorney, Agent, or Firm* — Turocy & Watson, LLP

(57) ABSTRACT

Bacterial lipopolysaccharide (LPS) in systemic circulation triggers deleterious super-inflammatory response, which is key pathogenesis of many disorders like gram-negative sepsis and necrotizing enterocolitis. No effective therapeutic interventions are currently available for protection of patients against mortality. Disclosed are methods and therapeutic agents that ablate the biological toxicity of LPS in circulation (Integrin Peptide), and abrogate leukocyte infiltration into lung and liver and suppress adhesion molecule expression (Integrin Peptide and Anti-CD18 βA scFv). These therapeutic agents can be used alone, or in combination for treatment of endotoxin-mediated pro-inflammatory responses, particularly in cases of acute sepsis and necrotizing enterocolitis.

12 Claims, 13 Drawing Sheets

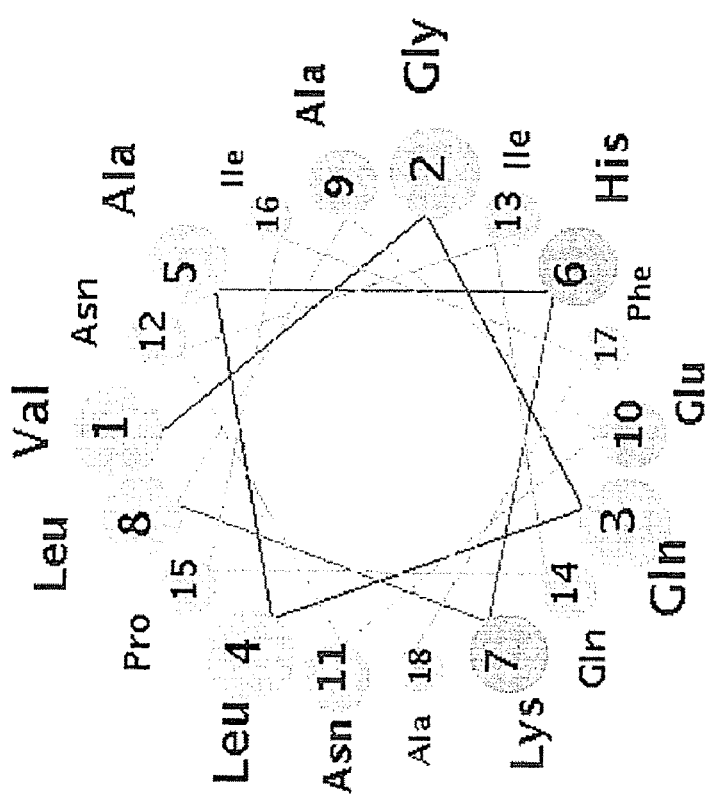
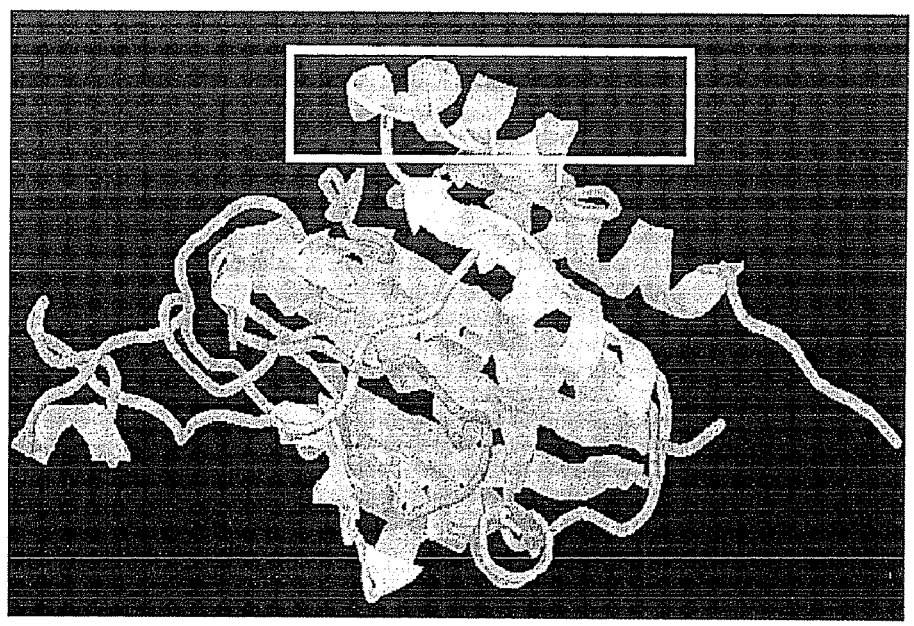
Figure 1B

Figure 2

Polypeptide sequence of anti-CD18 βA scFv (SEQ ID NO.3)

V_H Domain

```
V K L Q Q S G T E V V K P G A S V K L S
C K A S G Y I F T S Y D I D W V R Q T P
E Q G L E W I G W I F P G E G S T A Y N
E K F K G R A T L S V D K S S T A Y M
E L T R L T S E D S A V Y F C A R G D Y
T Y R Y F D L W G Q G T T V T V S S C
```

Linker: G G G G S G G G G S G G G G S

V_L Domain

```
S D I E L T Q S P A I M S A S P G E R V
T M T C S A S S S I R Y I Y W Y Q Q K P
G S S P R L L I Y D T S N V A P G V P F
R F S G S G S G T S Y S L T I N R M E A
E D A A T Y Y C Q E W S G Y P Y T F G G
```

GAPVPYPDPLEPR — 13 amino acid-peptide E tag

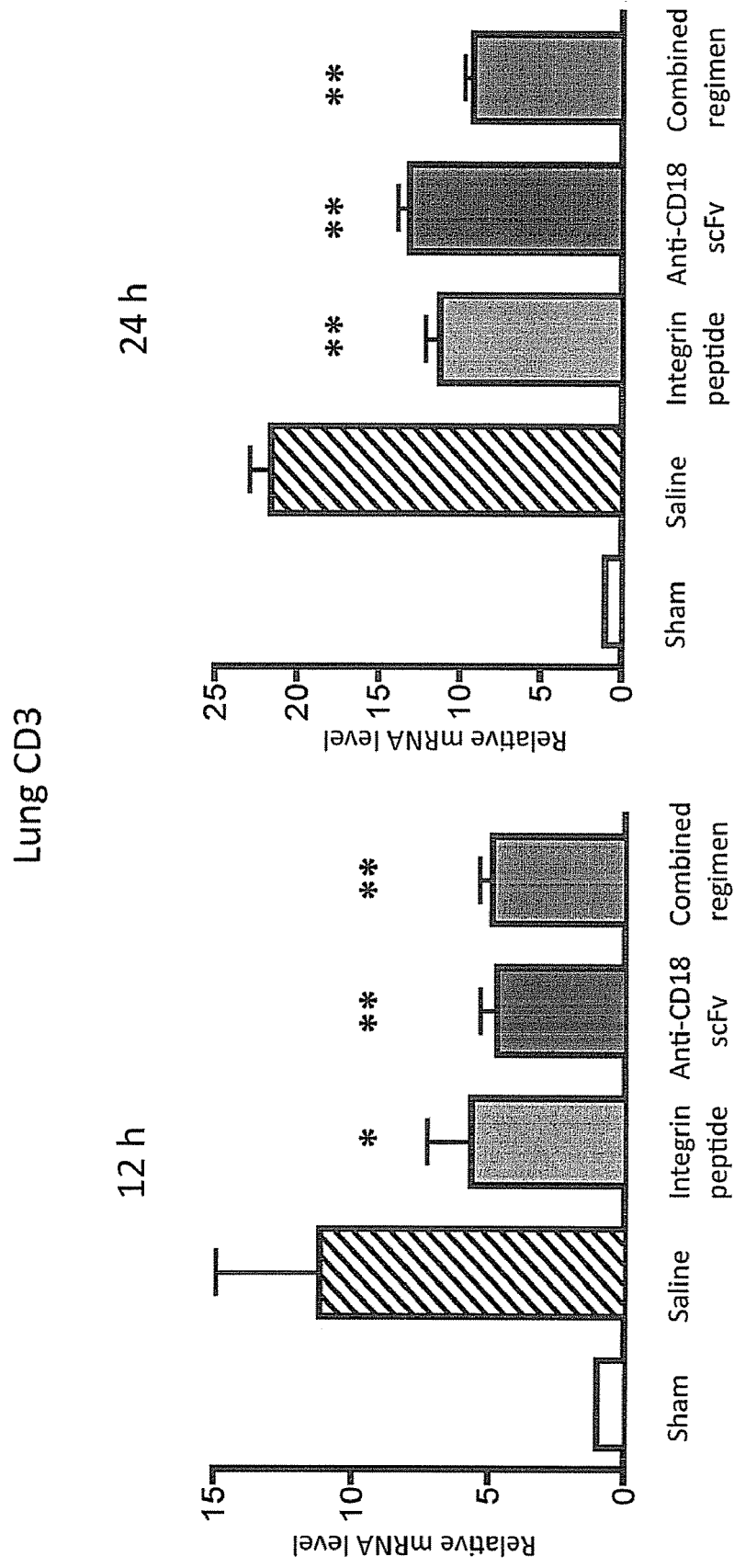

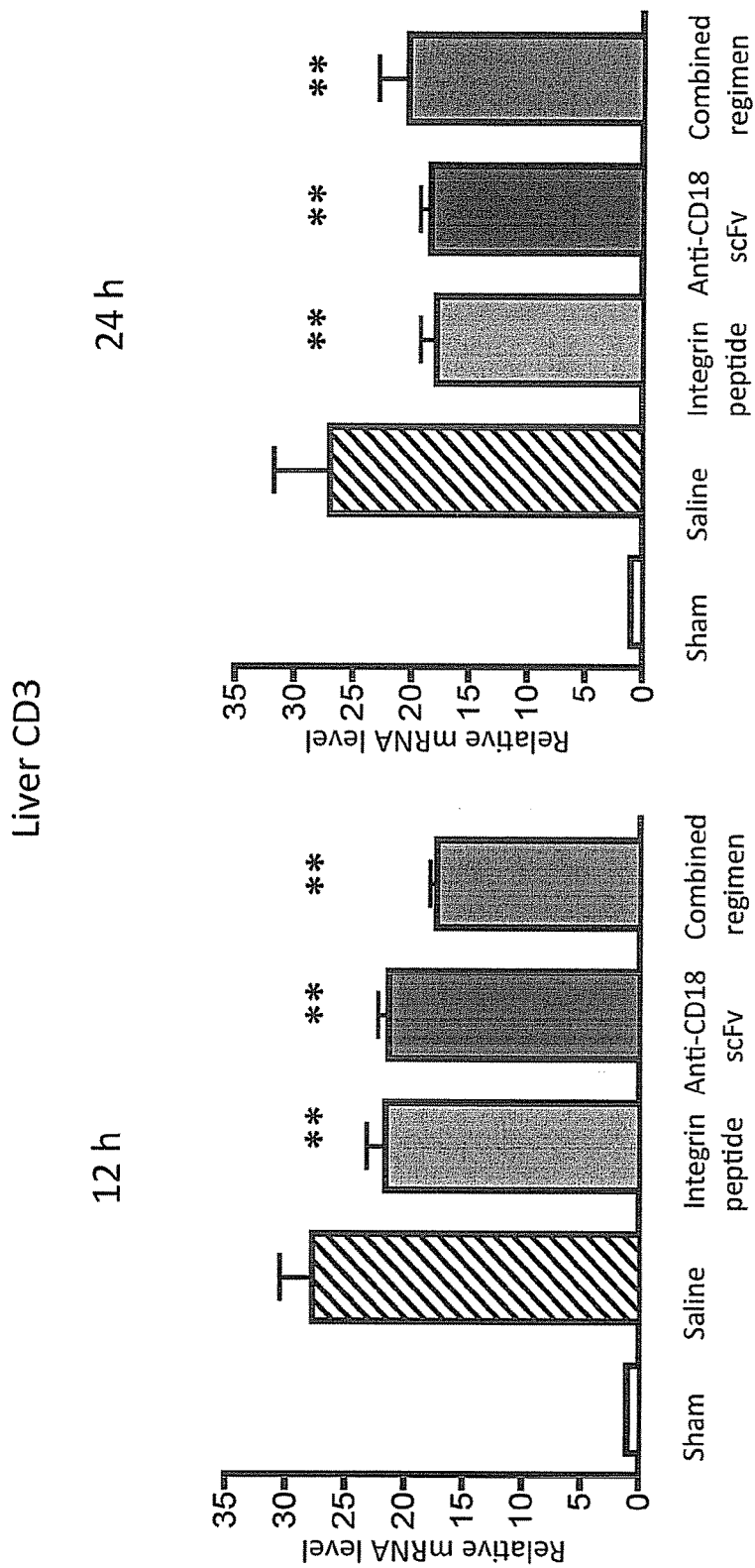

METHODS AND COMPOSITIONS FOR TREATMENT OF ENDOTOXIN-MEDIATED PRO-INFLAMMATORY RESPONSES

CROSS-REFERENCE TO RELATED APPLICATIONS

This application claims the benefit of priority to Provisional Application Ser. No. 61/080,558 filed on Jul. 14, 2008, which is incorporated herein by reference.

TECHNICAL FIELD

This disclosure relates to methods and compositions for treatment of endotoxin-mediated pro-inflammatory responses, and more specifically to the treatment of acute peritonitis and sepsis conditions. Artificial single-chain anti-CD18 βA antibodies (anti-CD18 βA) and novel Integrin peptides are disclosed for use in the treatment of endotoxin-mediated pro-inflammatory responses.

BACKGROUND

Critically-ill patients suffering from acute sepsis are at immediate risk of death. The current management approaches for these patients depend on the use of corticosteroids, antibiotics, fluid resuscitation, and supportive care for failing organs. However, these interventions are not efficacious enough to achieve a 100% protection of patients against organ failures and death. The mortality rate of patients with severe sepsis is about 50%, and can reach 90% if septic shock results.

Bacterial lipopolysaccharide (LPS) is a structural component of the outer cell membrane of the bacterial cell wall. Once being released in circulation, free and biological active LPS molecules stimulate monocytic cells to release pro-inflammatory cytokines. Controlled and localized releases of these cytokines help the host immunity to mount inflammatory responses to get rid of the invading pathogenic bacteria. However, in response to severe overwhelming bacterial infection, un-checked and widespread releases of pro-inflammatory cytokines can result in deleterious activation of coagulation systems and leukocyte-mediated reactions that ultimately lead to multiple organ failure and even death. Hyper-activation on the coagulation leads to thrombosis, tissue hypoxia, and necrosis. Meanwhile, extravasation and tissue infiltration of inflammatory leukocytes are also stimulated. The infiltrated leukocytes cause tissue damages by many different cellular mechanisms like generation of reactive oxygen species which damage the plasma membrane.

Based on the current understanding of sepsis pathogenesis, therapeutic agents that are able to reduce the release of pro-inflammatory cytokines through blocking the initial LPS stimulation on the host immune system, and/or the infiltration of leukocytes into tissues are likely to benefit the survival of patients with acute sepsis.

Thus there remains a need for additional therapeutics for treatment of critically ill patients with acute peritonitis and sepsis in emergency units.

SUMMARY

The subject invention pertains to methods of treatment of endotoxin-mediated pro-inflammatory response, and to novel therapeutic agents and the use of these agents in, for example, treatment of the adverse effects of inflammation, including the severe tissue damage that can occur in patients suffering from sepsis. Leukocyte $\beta_2$ integrins are believed to serve as receptors for LPS that mediate the pro-inflammatory response. Leukocyte $\beta_2$ integrins are heterodimers in which a β subunit (CD18) pairs with at least four distinct α subunits (CD11a, CD11b, CD11c, and CD11d).

Disclosed herein are a novel Integrin Peptide and an anti-CD18 βA scFv antibody useful as therapeutic agents to protect against adverse effects, including mortality, associated with inflammation caused by endotoxins including LPS.

In specific embodiments, the present invention is directed to the use of Integrin Peptide and/or anti-CD18 βA scFv in the protection of animals including humans, against acute sepsis.

Thus, in an embodiment, the subject invention provides a single-chain antibody targeting to the CD18 βA domain (anti-βA domain ScFv). In contrast to conventional therapeutic antibodies, the ScFv molecule of the subject invention is an antibody that contains the variable regions of light and heavy chains joined together with a flexible linker, but is without the constant region (Fc). The absence of a constant region allows better tissue penetration, lower immunogenicity and higher specificity.

In another embodiment, Integrin Peptide is able to ablate the biological activity of endotoxin in circulation. Additionally, administration of Integrin Peptide and anti-CD18 βA scFv, either individually or in combined regimen, can be used to suppress pro-inflammatory cytokine releases, adhesion molecule expression, and leukocyte infiltration into tissues.

Another embodiment of the invention is a method for screening for compounds which may inhibit or ameliorate endotoxin-mediated pro-inflammatory response comprising assessing the avidity of a candidate compound for binding a CD18 βA domain. In related methods, the assessment is by using a competitive binding assay and assessing the displacement by a candidate compound of anti-CD18 βA scFv or a conservative variant or fragment thereof bound to CD18 βA domain.

In other related methods, the CD18 βA domain is $\beta A_{266-318}$. Preferred candidates will be observed to have equal or superior binding specificity to CD18 βA domain as does anti-CD18 βA scFv of the subject invention.

Yet another aspect of the invention is inhibiting the binding of LPS to CD18 βA domain, either in vitro or in vivo. In related methods, the inhibition is accomplished by administration of either Integrin Peptide, anti-CD18 βA, or a combination of both.

Still other embodiments of the invention include isolated polynucleotides encoding Integrin Peptide, anti-CD18 βA, and fragments thereof sufficient to retain the LPS-to-CD18 βA binding inhibition character of the peptides having the sequences of SEQ ID NO.1 and SEQ ID NO.3. Such fragments are easily and routinely generated by, for example, use of Bal31 exonuclease for time-controlled, limited digestion from the ends of starting polynucleotides.

BRIEF DESCRIPTION OF THE FIGURES

FIG. 1B is a graphic presentation of a polypeptide sequence (SEQ ID NO. 1) and an in silico model of the Integrin peptide. The helical arrangement of integrin peptide is depicted by a helical wheel diagram as shown. The helix demonstrates features of an amphipathic helix.

FIG. 2 is a graphic presentation of a polypeptide sequence (SEQ ID NO. 3) of the anti-CD18 βA scFv selected from a scFv cDNA library that was displayed by bacteriophage in accordance with an embodiment of the invention. Underlined are the complementarity-determining regions (CDR) of the antibody as predicted by Kobat's algorithm. The variable domains of the heavy and light immunoglobulin chains, designated as $V_H$ and a $V_L$, respectively, are joined to form anti-CD18 βA scFv by a linker. The linker consists of three repeated units of (Gly)$_4$Ser. At the C-terminal end of the anti-CD18 βA scFv, (SEQ ID NO. 3) a 13 amino acid-peptide E tag is linked.

FIG. 6 is a graphic presentation of the result of CD3 mRNA real-time PCR for the effect of Integrin Peptide, anti-CD18 βA scFv, and combined regiment on the infiltration of leukocytes into (A) lung and (B) livers of the CLP-inflicted mice.

BRIEF SUMMARY OF THE SEQUENCES

Figure 1A:
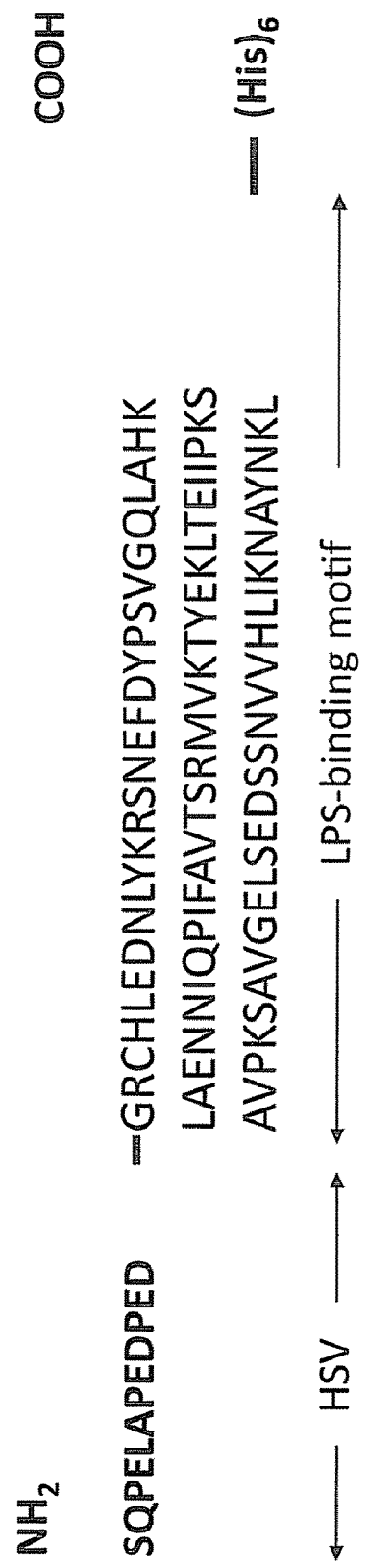
FIG. 1A shows the amino acid sequence for an Integrin peptide (SEQ ID NO. 1) in accordance with an embodiment of the invention.

SEQ ID NO. 1 is the polypeptide sequence of Integrin Peptide.

SEQ ID NO. 2 is a polynucleotide sequence encoding Integrin Peptide.

SEQ ID NO. 3 is the polypeptide sequence of anti-CD18 βA scFv.

SEQ ID NO. 4 is the nucleotide sequence of anti-CD18 βA scFv.

SEQ ID NO. 5 is the polypeptide sequence of a $V_H$-derived region of anti-CD18 βA scFv.

SEQ ID NO. 6 is the polypeptide sequence of a $V_L$-derived region of anti-CD18 βA scFv.

SEQ ID NO. 7 is the polypeptide sequence of a CDR of anti-CD18 βA scFv.

SEQ ID NO. 8 is the polypeptide sequence of a CDR of anti-CD18 βA scFv.

SEQ ID NO. 9 is the polypeptide sequence of a CDR of anti-CD18 βA scFv.

SEQ ID NO. 10 is the polypeptide sequence of a CDR of anti-CD18 βA scFv.

SEQ ID NO. 11 is the polypeptide sequence of a CDR of anti-CD18 βA scFv.

SEQ ID NO. 12 is the polypeptide sequence of a CDR of anti-CD18 βA scFv.

DETAILED DESCRIPTION

The subject invention pertains to novel therapeutic agents and the use of these agents in, for example, treatment of the adverse effects of inflammation, including the severe tissue damage that can occur in patients suffering from sepsis.

The terms "treatment" and "therapy" are used interchangeably herein, and as used herein include both prophylactic and responsive treatment, can be either acute short-term or chronic long-term, and denote the inhibition or amelioration of an inflammatory or immune response in a patient. "Patient" includes animals including mammals and humans. "Ameliorate" or "amelioration" denotes a lessening of the detrimental effect of the inflammatory or immune response disorder in the patient receiving therapy. The term "therapeutically effective" means that the amount of therapeutic agent (Integrin Peptide, anti-CD18 βA scFv, or a combination of those) used is of sufficient quantity to inhibit or ameliorate the symptoms of inflammatory or immune response.

Some embodiments of the invention relate to a single-chain antibody having affinity for the CD18 βA domain antigen (anti-βA domain ScFv). In contrast to conventional therapeutic antibodies, the embodiments of the ScFv antibody contain the variable regions of the light and heavy chains joined together with a flexible linker in a single polypeptide sequence—rather than constituent parts of two separate polypeptide sequences—without a constant region (Fc). The absence of a constant region allows better tissue penetration, lower immunogenicity and higher specificity.

In one embodiment, Integrin Peptide is able to ablate the biological activity of endotoxin in circulation in the blood and other bodily fluids. Additionally, administration of anti-CD18 βA scFv, either individually or in combination with an Integrin peptide, as will be discussed below, can be used to suppress pro-inflammatory cytokine releases, adhesion molecule expression, and leukocyte infiltration into tissues.

Another embodiment of the invention is a method for screening for compounds which may inhibit or ameliorate endotoxin-mediated pro-inflammatory response comprising assessing the avidity of a candidate compound for binding a CD18 βA domain. In related methods, the assessment is by using a competitive binding assay and assessing the displacement by a candidate compound of anti-CD18 βA scFv or a conservative variant or fragment thereof bound to CD18 βA domain.

In other related methods, the CD18 βA domain at least consists of residues 266-318 ($βA_{266-318}$) of human CD18 βA domain (SEQ ID NO.7). Preferred candidates will be observed to have equal or superior binding specificity to CD18 βA domain as does anti-CD18 βA scFv of the subject invention.

Yet another aspect of the invention is inhibiting the binding of LPS to CD18 βA domain, either in vitro or in vivo. In related methods, the inhibition is accomplished by administration of either an Integrin Peptide, anti-CD18 βA scFv, or a combination of both.

Still other embodiments of the invention include isolated polynucleotides encoding Integrin Peptide, anti-CD18 βA, and fragments thereof sufficient to retain the LPS-to-CD18 βA binding inhibition character of the peptides having the sequences of SEQ ID NO.1 and SEQ ID NO.2. Such fragments are easily and routinely generated by, for example, use of Bal31 exonuclease for time-controlled, limited digestion from the ends of stating polynucleotides.

Some embodiments of the invention relate to an Integrin Peptide, that can be recombinantly-produced, whose amino acid sequence has been derived from one of the LPS-binding sites on the CD18 βA domain. That is, the Integrin Peptide is derived from regions of the CD18 βA receptor protein identified as having affinity for LPS. The Integrin Peptide binds LPS readily, and antagonizes LPS action in vitro.

Anti-CD18 βA scFv is a variable fragment, that can be recombinantly-produced, whose epitope is located in the CD18 βA domain. Anti-CD18 βA scFv recognizes mammalian integrins in both of resting and activated conformations.

The dosage ranges for the administration of the therapeutic agents of the invention are those large enough to produce the desired effect in which the symptoms of the endotoxin mediated disorder are treated. The dosage should not be so large as to cause adverse side effects, such as unwanted cross-reactions, anaphylactic reactions, and the like. Generally, the dosage will vary with the age, condition, sex and extent of the symptoms in the patient and can be determined by one of skill in the art. The dosage can be adjusted by the individual physician in the event of any counter-indications. The dosage amount depend on the specific endotoxin mediated condition which is treated and can be readily determined using known dosage adjustment techniques by a physician having ordinary skill in treatment of these disorders. The dosage amount will generally lie within an established therapeutic window for the therapeutic compound which will provide a therapeutic effect while minimizing additional morbidity and mortality. Typically, therapeutic compounds will be administered in a dosage ranging from 0.001 mg/kg to about 100 mg/kg per dose, preferably 0.1-20 mg/kg. The preferred dose of about 0.5-5 mg/kg is particularly useful for compounds containing the therapeutic agents disclosed herein, in one or more dose administrations daily, for one or several days.

Any of the compositions described herein may be formulated for pharmacological or therapeutic administration either to a mammal, or more preferably to a human. As such, the compositions may be contained in a pharmaceutically acceptable carrier. The preferred mode of administration of a peptide active agent is by injection, either intravenous, intra-arterial, intramuscular or subcutaneous. Other routes of administration may also be possible and would be included within the scope of the present disclosure.

The compositions can be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Definitions

A term "variant" polypeptide or polynucleotide refers herein to a molecule which differs in amino acid or nucleotide sequence from a "parent" polypeptide or polynucleotide sequence by virtue of addition, deletion and/or substitution of one or more amino acid residue(s) in the parent sequence. A variant polypeptide or polynucleotide possesses a similar or identical function to the parent polypeptide or polynucleotide. A variant polypeptide has a similar amino acid sequence to a parent polypeptide and satisfies at least one of the following: polypeptide having an amino acid sequence that is one or more of at least about 40%, at least about 50%, at least about 60%, at least about 70%, at least about 80%, at least about 90%, at least about 95%, and at least about 98% identical and/or conservatively substituted. A variant polynucleotide has a similar amino acid sequence to a parent polynucleotide and satisfies at least one of the following: (i) a polypeptide encoded by a variant nucleotide sequence is one or more of at least about 40%, at least about 50%, at least about 60%, at least about 70%, at least about 80%, at least about 90%, at least about 95%, and at least about 98% identical to the parent polypeptide; or (ii) a variant polynucleotide sequence hybridizes under stringent conditions as defined herein to a parent polynucleotide sequence.

An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular materials, or culture medium when produced by recombinant techniques, or substantially free of chemical precursors or other chemicals when chemically synthesized, but excludes nucleic acid molecules present in recombinant DNA libraries. In a preferred embodiment of the invention, nucleic acid molecules encoding polypeptides/proteins of the invention are isolated or purified.

The term "under stringent condition" refers to hybridization and washing conditions under which nucleotide sequences having homology to each other remain hybridized to each other. Such hybridization conditions are described in, for example but not limited to, *Current Protocols in Molecular Biology*, John Wiley & Sons, N.Y. (1989), 6.3.1-6.3.6.; *Basic Methods in Molecular Biology*, Elsevier Science Publishing Co., Inc., N.Y. (1986), pp. 75-78, and 84-87; and *Molecular Cloning*, Cold Spring Harbor Laboratory, N.Y. (1982), pp. 387-389, and are well known to those skilled in the art. A preferred, non-limiting example of stringent hybridization conditions is hybridization in 6× sodium chloride/sodium citrate (SSC), 0.5% SDS at about 68° C. followed by one or more washes in 2×SSC, 0.5% SDS at room temperature. Another preferred, non-limiting example of stringent hybridization conditions is hybridization in 6×SSC at about 45° C. followed by one or more washes in 0.2×SSC, 0.1% SDS at about 50-65° C.

"Conservatively substituting" or "conservative substitution" of amino acid residues refers to substitution of amino acid residues in a parent polypeptide with amino acid residues with similar chemical properties and/or physical properties to form a variant polypeptide. An amino acid residue can belong to any of the following 10 chemical groups, where substituting any amino acid residue with another amino acid residue from the same chemical group is a conservative substitution: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; (4) neutral nonpolar (hydrophobic) amino acids such as alanine, leucine, isoleucine, valine, proline, phenylalanine, tryptophan, and methionine; (5) amino acids having aliphatic side chains such as glycine, alanine, valine, leucine, and isoleucine; (6) amino acids having aliphatic-hydroxyl side chains such as serine and threonine; (7) amino acids having amide-containing side chains such as asparagine and glutamine; (8) amino acids having aromatic side chains such as phenylalanine, tyrosine, and tryptophan; (9) amino acids having basic side chains such as lysine, arginine, and histidine; (10) amino acids having sulfur-containing side chains such as cysteine and methionine.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Embodiments of the Invention

The anti-CD18 βA scFv antibody and Integrin peptide disclosed herein are both polypeptides that can take the form of either a specific sequence disclosed herein or a variant of a sequence disclosed herein. A polypeptide can be formulated into a composition in a neutral or salt form. Pharmaceutically acceptable salts, include the acid addition salts (formed with the free amino groups) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

The invention also relates to a method for preparing a medicament or pharmaceutical composition comprising the therapeutic agents of the invention, the pharmaceutical composition being used for therapy of endotoxin-mediated pro-inflammatory response and resulting disorders.

The therapeutic effects of these two novel agents, anti-CD18 βA scFv and Integrin peptide, have been assessed in a well-known murine cecal ligation and puncture (CLP) model. Integrin Peptide was found to be able to ablate the biological activity of endotoxin in circulation. Studies showed that the Integrin Peptide, anti-CD18 βA scFv, and a combined regimen of Integrin Peptide and anti-CD18 βA scfv were able to suppress the peritonitis-induced releases of pro-inflammatory cytokines and expression of ICAM-1 in the liver. Integrin Peptide also was able to suppress the VCAM and E-selectin expression in lung of the CLP-inflicted mice. Infiltration of leukocytes into the lung and liver was also found to be reduced by treatment with these novel therapeutics.

The therapeutic effect of Integrin Peptide has also been examined in a well-established rat model of necrotizing enterocolitis (NEC) in addition to the CLP model. In rat the NEC model, super-inflammatory response is induced by bacterial LPS that is infused into the rat jejunum. Integrin peptide was able to suppress the NEC-induced releases of pro-inflammatory cytokines and expression of the innate immunity components including TLR4, CD14, and MD-2.

In certain embodiments, this invention relates to novel therapeutic agents having ability to improve survival of human patients at risk for, or suffering from, acute sepsis.

A. Integrin Peptide

The binding of LPS to its cellular receptors initiates the pro-inflammatory signaling cascade. The pathogen associated molecular patterns (PAMPs), including LPS, are recognized by a family of receptors termed toll-like receptors (TLRs). TLR4 recognizes LPS, and the binding of LPS to TLR4 leads to activation of signaling pathways which are mediated by various transcriptional regulators. Nuclear factor-κB is one of the many important regulators, and its translocation from cytoplasm to nucleus can result in transcription of many pro-inflammatory cytokines including TNF-α.

In order to reduce or cease the production of pro-inflammatory cytokines, experimental agents that attempted to block the LPS binding on TLR4 have been produced. Their protection efficacies have been assessed by many studies on laboratory animals and septic patients. Yet, few experimental agents resulted in satisfactory protection. The underlying reasons for the limited success are not clearly understood. Nevertheless, the immunogenicity of these antibodies and antagonists, of which origins are not human, might lead to immunologic reactions that potentially lead to undesirable clinical manifestations like allergic reactions.

From a practical point of view, the use of product derived from human proteins is advantageous as it prevents side-effects such as anaphylaxis caused by immune response. As such, the present invention introduces Integrin Peptide, which has a sequence derived from a LPS-binding site on the CD18 βA domain of human leukocyte integrins. Leukocyte integrins (CD11/CD18), referred as $β_2$ integrins, are receptors to bacterial LPS. Our recent epitope analysis on the CD18 antigen revealed two LPS-binding sites that are located at residues 216-248 and 266-318. Accordingly, the two binding sites are designated as $βA_{216-248}$ and $βA_{266-318}$. See Wong et al. (2007), *FASEB J.*, vol. 21, 3231-3239, which is incorporated herein by reference. Two recombinant peptides of the polypeptide sequences of these two binding sites were then produced, and the one derived from the $βA_{266-318}$ (Integrin Peptide) was found effective to inhibit LPS action on human lymphoblast cell line (Jurkat cells) in vitro.

In one embodiment, the Integrin peptide encompasses SEQ ID NO. 1 or a variant of SEQ ID NO. 1. In one embodiment, a variant of SEQ ID NO. 1 has about 70% or more identity and/or conservative substitution to SEQ ID NO. 1. In another embodiment, a variant of SEQ ID NO. 1 has about 80% or more identity and/or conservative substitution to SEQ ID NO. 1. In yet another embodiment, a variant of SEQ ID NO. 1 has about 90% or more identity and/or conservative substitution to SEQ ID NO. 1. In still yet another embodiment, a variant of SEQ ID NO. 1 has about 95% or more identity and/or conservative substitution to SEQ ID NO. 1.

B. Anti-CD18 βA scFv

Leukocyte integrins, in which a common CD18 antigen pairs with at least four distinct CD11 antigens, facilitate the extravasation and migration of inflammatory leukocytes into tissues. To promote the movements, integrins interact with different cellular adhesion molecules. The major binding ligands for leukocyte integrins are intercellular adhesion molecules (ICAMs). In view of this, any antagonists that disrupt the interaction between integrins and ICAMs are likely to reduce the infiltrating process so as to result in less tissue damage during sepsis.

In this context, monoclonal antibodies specifically targeted to either CD11 or CD18 antigen of leukocyte integrins were generated by the traditional hybridoma technology, with an initial attempt to block the integrin/ICAMs interactions. Despite the reported reduced severity of sepsis in laboratory animals and patients, the pharmacokinetics of these monoclonal antibodies is indeed limited by the presence of the constant region ($F_C$). The presence of the $F_C$ renders an antibody with a molecular mass of approximate 150 kDa, a mass that is high enough to hinder effective tissue penetration of the antibody. In addition, the interactions between the $F_C$ and its respective receptors distributed throughout the body can lead to undesirable biodistribution of the therapeutic antibody. More importantly, the $F_C$ can be immunogenic to patients, causing undesirable clinical outcomes.

In order to reduce infiltration of inflammatory leukocyte into tissues, and to circumvent the general problems encountered with the use of traditional therapeutic antibody, the present invention exploits the use of a single-chain antibody (scFv) that targets to the CD18 βA domain. The scFv consists of the antigen-binding sites ($V_H$ and $V_L$) of heavy and light chains, which are joined by a linker, and is absent the $F_C$ portion. The relative low molecular mass of scFv allows its efficacious penetration into tissue. The problems of immunogenicity and undesirable biodistribution are also circumvented.

The scFv produced in the present invention targets to the leukocyte CD18 βA domain. Many functional and site-directed mutagenesis studies have revealed the CD18 βA domain is important in ligand recognition for interaction between integrins and adhesion molecules. In view of this, a scFv binding to the CD18 βA domain with high avidity has been generated. A phage-displayed library consisting of a population of scFv-coding cDNA fragment was constructed. After the three-round panning, a high-avidity clone was finally selected. The binding property of the anti-CD18 βA scFv was verified by immunoprecipitation, and the FASC analysis of the binding of anti-CD18 βA scFv to different human lymphoblast cell lines shows the anti-CD18 βA scFv is able to bind integrins in both resting and activated conformations.

The structure of the anti-CD18 βA scFv antibody is shown in FIG. 2, as a single polypeptide chain. The anti-CD18 βA scFv antibody encompasses a polypeptide chain having at least three amino acid sequences present: i) a sequence derived from a $V_H$ domain (SEQ ID NO. 5); ii) a flexible linker sequence; and iii) a sequence derived from a $V_L$ domain (SEQ ID NO. 6). The sequence derived from the $V_H$ domain is located toward the N-terminus of the anti-CD18 βA scFv antibody relative to the sequence derived from the $V_L$ domain with the flexible linker sequence intermediate between the $V_H$ and $V_L$ domain sequences. The precise identity of the flexible linker sequences is not believed to be critical. In one embodiment, the linker sequence is about 60% or more glycine residues. In another embodiment, the linker sequence is about 75% or more glycine residues. In one embodiment, the linker sequence is two or more repeating units of Gly-Gly-Gly-Gly-Ser. In one embodiment, the linker sequence is from about 8 to about 25 residues in length.

The anti-CD18 βA scFv antibody encompasses a SEQ ID NO. 5 or a variant of SEQ ID NO. 5, where the term "variant" is defined above. In one embodiment, a variant of SEQ ID NO. 5 has about 70% or more identity and/or conservative substitution to SEQ ID NO. 5. In another embodiment, a variant of SEQ ID NO. 5 has about 80% or more identity and/or conservative substitution to SEQ ID NO. 5. In yet another embodiment, a variant of SEQ ID NO. 5 has about 90% or more identity and/or conservative substitution to SEQ ID NO. 5. In still yet another embodiment, a variant of SEQ ID NO. 5 has about 95% or more identity and/or conservative substitution to SEQ ID NO. 5.

In addition, the anti-CD18 βA scFv antibody encompasses a SEQ ID NO. 6 or a variant of SEQ ID NO. 6, where the term "variant" is defined above. In one embodiment, a variant of SEQ ID NO. 6 has about 70% or more identity and/or conservative substitution to SEQ ID NO. 6. In another embodiment, a variant of SEQ ID NO. 6 has about 80% or more identity and/or conservative substitution to SEQ ID NO. 6. In yet another embodiment, a variant of SEQ ID NO. 6 has about 90% or more identity and/or conservative substitution to SEQ ID NO. 6. In still yet another embodiment, a variant of SEQ ID NO. 6 has about 95% or more identity and/or conservative substitution to SEQ ID NO. 6.

In one embodiment, the anti-CD18 βA scFv antibody encompasses SEQ ID NO. 3 or a variant of SEQ ID NO. 3. In one embodiment, a variant of SEQ ID NO. 3 has about 70% or more identity and/or conservative substitution to SEQ ID NO. 3. In another embodiment, a variant of SEQ ID NO. 3 has about 80% or more identity and/or conservative substitution to SEQ ID NO. 3. In yet another embodiment, a variant of SEQ ID NO. 5 has about 90% or more identity and/or conservative substitution to SEQ ID NO. 3. In still yet another embodiment, a variant of SEQ ID NO. 3 has about 95% or more identity and/or conservative substitution to SEQ ID NO. 3.

SEQ ID NO. 5 and SEQ ID NO. 6 contain complementary determination regions (CDRs) that are believed to be involved in recognition of the CD18 βA epitope. CDRs are shown underlined in FIG. 2. In one embodiment, SEQ ID NO. 5 or a variant of SEQ ID NO. 5 encompasses the sequence SYDID (SEQ ID NO. 12). In another embodiment, SEQ ID NO. 5 or a variant of SEQ ID NO. 5 encompasses SEQ ID NO. 7 or a variant of SEQ ID NO. 7 having 70% or more identity. In yet another embodiment, SEQ ID NO. 5 or a variant of SEQ ID NO. 5 encompasses SEQ ID NO. 7 or a variant of SEQ ID NO. 8 having 70% or more identity.

In one embodiment, SEQ ID NO. 6 or a variant of SEQ ID NO. 6 encompasses SEQ ID NO. 9 or a variant of SEQ ID NO. 9 having 70% or more identity. In another embodiment, SEQ ID NO. 6 or a variant of SEQ ID NO. 6 encompasses SEQ ID NO. 10 or a variant of SEQ ID NO. 10 having 70% or more. identity. In yet another embodiment, SEQ ID NO. 6 or a variant of SEQ ID NO. 6 encompasses SEQ ID NO. 11 or a variant of SEQ ID NO. 11 having 70% or more identity.

Efficacy Study in Animal Models of Acute Peritonitis

The efficacy of Integrin Peptide and anti-CD18 βA scFv in protecting animals against acute peritonitis has been assessed in experiments using a well-known murine model referred to as cecal ligation and puncture (CLP). CLP is a stringent model of human sepsis. In this model, cecum of mouse was non-obstructively ligated and punctured with 19-gauge needle twice. Intestinal bacterial flora then contaminates the peritoneal cavity, and triggers immunological reactions that are analogous to the septic responses of human sepsis. Results showed that treatment of the CLP-inflicted mice with Integrin Peptide and anti-CD18 βA scFv, either individually or in combined regimen, resulted in reduction of the pro-inflammatory responses as shown by the lowered pro-inflammatory cytokine releases and leukocyte infiltration into tissues. Significant increases in the 48-hour survival rate were also noted among mice treated with the novel therapeutics.

The therapeutic efficacy of Integrin Peptide in protecting animals against endotoxin-mediated hyper-inflammatory response has also been assessed in a rat model of necrotizing enterocolitis. In this model, the jejunum of rat is distended with bacterial LPS, and this distention induces hyper-inflammatory reaction as being reflected by increases in circulating pro-inflammatory cytokines. The expression of the innate immunity components is elevated as well. Results showed that treatment with NEC rats with Integrin Peptide reduced the inflammatory response toward bacterial LPS.

Collectively, the instant specification discloses methods of inhibiting endotoxin-mediated pro-inflammatory responses, exemplified herein by amelioration of hyper-inflammatory response of sepsis and necrotizing enterocolitis. Also disclosed are methods of preparation of the Integrin Peptide and anti-CD18 βA scFv. In particular, methods of use of these two therapeutics in treatment of animals, including humans, are also taught herein. Our results show that Integrin Peptide and anti-CD18 βA scFv are lead molecules that can be used as novel interventions for treatment of acute sepsis, as well as other endotoxin-mediated pro-inflammatory responses.

The Integrin Peptide of the subject invention can be a recombinantly produced peptide comprising the following amino acid sequence that is derived from a newly found LPS binding site along the leukocyte CD18 βA domain antigen, viz. residues 266-318:

```
                                                    (SEQ ID NO. 1)
GRCHLEDNLYKRSNEFDYPSVGQLAHKLAENNIQPIFAVTSRMVKTYEKL

TEIIPKSAVPKSAVGELSEDSSNVVHLIKNAYNKL (Wong K F et.
al., 2007).
```

The anti-CD18 βA scFv herein is an antibody, preferably recombinantly produced, that targets to the CD18 βA domain, and was originally selected from a phage-displayed cDNA library.

EXAMPLES

Practical of aspects of the present invention are illustrated in the following examples. Example 1 illustrates the procedures of the preparation of Integrin Peptide and anti-CD18 βA scFv recombinantly using a prokaryotic bacterial expression system. Example 2 illustrates the in vivo study of the protection conveyed by Integrin Peptide and anti-CD18 βA scFv on mice against endotoxin-mediated tissue damages and lethality, using a well-known murine model termed cecal ligation and puncture model. Example 3 addresses the serological analysis for the effect of Integrin Peptide on the biological activity of endotoxin in circulation using limulus amoebocyte (LAL) assay. Example 4 addresses the serological analysis for the effect of Integrin Peptide and anti-CD18 βA scFv on the serum level of TNF-α and IL-6 of the CLP-inflicted mice. Example 5 addresses the CD3 expression analysis for leukocyte infiltration into lung and livers. Example 6 addresses the analysis for the effect of Integrin Peptide and anti-CD18 βA scFv on the ICAM-1 transcript level in livers of the CLP-inflicted mice. This example addresses also the immunohistochemical analysis for the effect of Integrin Peptide on VCAM and E-selectin expression in lung. Example 7 addresses the effect of Integrin Peptide on the pro-inflammatory cytokine releases and the innate immunity of rat model of NEC. Example 8 addresses the assays screening candidate compounds that bind CD18 βA. Example 9 addresses the standard techniques of designing derivative structures can be used to produce candidates to be tested for enhanced inhibitory capacity.

Following are examples that illustrate procedures for practicing the invention. These examples should not be construed as limiting. All percentages are by weight and all solvent mixture proportions are by volume unless otherwise noted. Those of skill in the art should, in light of the present disclosure, appreciate that many changes can be made in the specific embodiments which are disclosed and still obtain a like or similar result without departing from the spirit and scope of the invention.

Example 1

A. Preparation of Integrin Peptide

Integrin Peptide is a polypeptide that was recombinantly produced and purified from a prokaryotic expression system. The preparation procedure for Integrin Peptide followed procedures that have been described (Wong K F, et al., 2007). In brief, the peptide-coding cDNA, 5'-ACCCCCAACGACG-GCCGCTGTCACCTGGAGGACAACTTGTA-CAAGAGGAGCAAC GAATTCGACTACCCATCG-GTGGGCCAGCTGGCGCACAAGCTGGCTGAAAACAACAT CCAGCCCATCTTCGCGGTGACCAGTAG-GATGGTGAAGACCTACGAGAAACTCACCG AGAT-CATCCCCAAGTCAGCCGTGGGGGAGCT-GTCTGAGGACTCCAGCAATGTGGTC CATCTCATTAAGAATGCTTACAATAAACTC-3' (SEQ ID NO.2) was amplified by polymerase chain reaction (PCR) using AmpliTaq Gold DNA polymerase. The DNA template used in PCR was a human CD18 cDNA construct, which was a generous gift from Dr. Lloyd B. Klickstein (Harvard Medical School, Boston, Mass., USA). The PCR conditions were in accordance with the manufacturer's instructions: 25 cycles of denaturation at 94° C. for 1 min, annealing at 55° C. for 30 sec and extension at 72° C. for 1 min. The resulting DNA fragment was purified, and cloned into an expression vector named pET43.1-B through two restriction sites: SacI and HindIII. Sequence-authenticated plasmid was then transformed into E. coli. of strain BL21 (DE3). Production of protein was induced by the addition of isopropyl-beta-D-thiogalactopyranoside to a final concentration of 0.5 mM. After an overnight incubation, bacterial cells were harvested by centrifugation at 3,000 g for 10 minutes and were subjected to sonication in lysis buffer (50 mM Tris-HCl, pH 8.0, 0.3 mM NaCl, 20 mM Imidazole). The recombinant Integrin Peptide contains a poly-histidine tag at its C-terminus, and it was purified from bacterial extracts using an immobilized affinity chromatography using the Ni-NTA column. Bound recombinant protein was eluted from column with 200 mM imidazole.

B. Preparation of Anti-CD18 βA scFv

Anti-CD18 βA scFv is an antibody that was recombinantly produced, and that targets to the CD18 βA domain of leukocyte integrins. To generate it, BALB/c mice were first immunized with purified recombinant CD18 βA domain, of which the production and purification was as described (Wong K F et. al., 2007). PCR amplification, cloning, protein production and purification were as the abovementioned. After immunization, spleens were surgically removed for extraction of total RNA. After reverse transcription, the variable genes of both heavy and light chains of immunoglobulin were amplified by polymerase chain reaction (PCR). Degenerate oligonucleotides were employed in the PCR as the sequences of the gene targets were not fully known. The resulting PCR products were purified and linked to give single-chain antibody cDNA fragments. These scFv cDNA fragments coded for antibody of a spectrum of avidity. A library of these cDNA clones was constructed. To select the clone that is showing pronounced avidity toward the CD18 βA domain, the library was infected with bacteriophages, and subjected to several rounds of panning. After three selection exercise, a cDNA clone whose scFv product demonstrated the highest avidity out of 40 clones was selected. The DNA sequence of this scFv clone was subsequently sequenced. Sufficient amount of the anti-CD18 βA scFv was prepared by a prokaryotic expression system. The expression and purification of the recombinant anti-CD18 βA scFv then followed the procedures that for the preparation of Integrin Peptide.

FIG. 2 shows the polypeptide sequence (SEQ ID NO.3), in which those underlined areas are the complementarity-determining regions (CDRs) of the antibody. The molecular architecture of anti-CD18 βA scFv was also predicted, in which the $V_H$ and $V_L$ domains are linking by a linker. The nucleotide sequence of the respective clone is SEQ ID NO. 4.

Example 2

Cecal Puncture and Ligation (CLP) Sepsis Model

The treatment of patients for protection against acute peritonitis by the subject therapeutics was assessed using a cecal ligation and puncture (CLP) model. The CLP model is one of the many stringent models that mimic the septic responses in human patients. In order to minimize possible variations that can arise from surgery, all surgical procedures were performed as described by Echtenacher B et al. by a single, board-qualified veterinary surgeon.

Before surgery, ICR mice were anesthetized with an intraperitoneal injection of 60 mg/kg sodium pentobarbital (Nembutal, Rhone Merieux, Pinkenba, QLD, Australia) in 0.3 ml sterile pyrogen-free saline. The cecum was exposed by a 15 mm midline incision of the anterior abdomen, and its distal end was ligated non-obstructively. The ligated cecum was then punctured by a 19-gauge needle twice. Punctured cecum was replaced back into the peritoneal cavity, and the incision was closed with clips. Mice of the sham-operated control group received laparotomy alone without any ligation and puncture of cecum.

At 2 hours after the surgery, treatments were administrated to mice by intraperitoneal injection. Mice were injected with either (i) sterile saline, (ii) Integrin Peptide (0.8 mg/kg), (iii) anti-CD18 βA scFv (0.8 mg/kg), and (iv) combined regimen of Integrin Peptide and anti-CD18 βA scFv (0.8 mg/kg for each agent). At 12 and 24 hours post-operative, mice receiving different treatments were sacrificed by cervical dislocation. Blood was then immediately drawn from the interior vena cava and stored at −20° C. until their uses in LAL assay and ELISA for the determination of endotoxin activity and pro-inflammatory cytokine levels, respectively. Frozen and paraffin-fixed liver samples were also collected for the real-time PCR and immunohistochemistry, respectively.

Survival Analysis of the CLP-Inflicted Mice

The protection of the CLP-mice against lethality by therapy with Integrin Peptide and anti-CD18 βA scFv has also been studied. Saline, Integrin Peptide, anti-CD18 βA scFv, and combined regimen-treated mice were monitored continuously for 48 hours after surgery. Mice that lived more than 48 hours were considered as survivors. Two independent experiments were performed, and data were analyzed with GraphPad Prism (GraphPad Software, Inc., La Jolla, Calif.).

Figure 3:
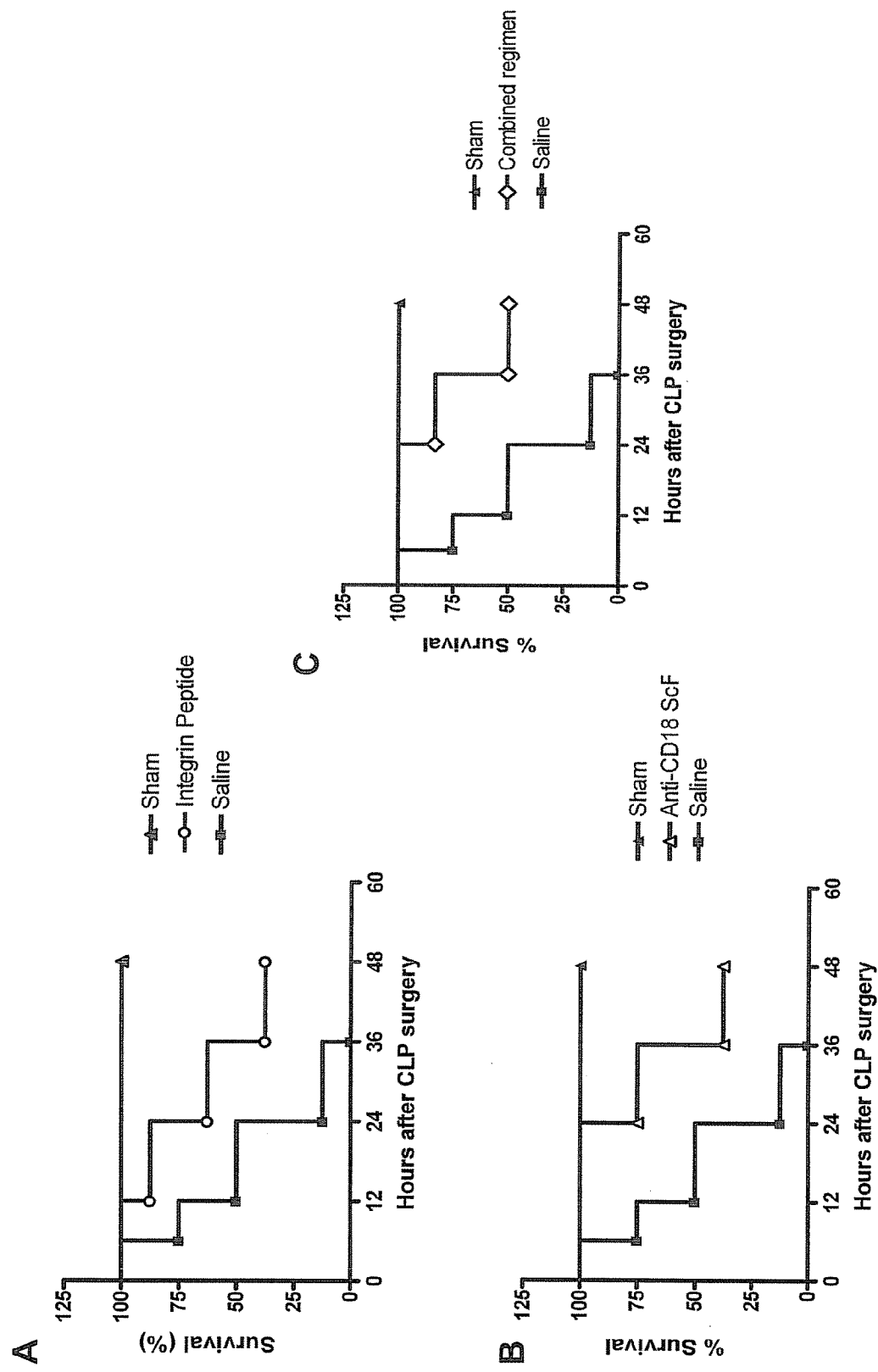
FIG. 3 is a graphic presentation of the result of survival analysis for the CLP-inflicted mice treated with (A) Integrin Peptide, (B) anti-CD18 βA scFv, and (C) a combined regimen.

Results of the survival analysis are presented in FIG. 3A-C. In the present study, none of the CLP-inflicted mice that were treated with saline survived longer than 36 hours post-operatively. The 48-hour survival rates of the CLP-inflicted mice treated with Integrin Peptide and anti-CD18 βA scFv were 37.5% and 37.5%, respectively. Combined regimen further increased the survival rate of CLP-inflicted mice to 50%. The survival benefits obtained from the therapeutic administration of Integrin Peptide and anti-CD18 βA scFv were all statistically significantly when compared to those treated with sterile saline.

Example 3

The effect of Integrin Peptide on the biological activity of endotoxin in circulation was determined by the LAL assay using the LAL pyrochrome kit (Associates of Cape Cod, Falmouth, Mass.) as previously described (Ho D W et al., *Asian J. Surg.* (2002), vol. 25, 73-39). All buffers for LAL assay were prepared by endotoxin-free water according to manufacturer's instruction. Signal development was monitored at optical density of 540 nm using microtiter plate reader (Molecular Devices, Sunnyvale, Calif.). Samples were analyzed in triplicate, and endotoxin levels were calculated from a standard curve with a dynamic range from 0 to 0.623 Endotoxin Units (EU)/ml.

Figure 4:
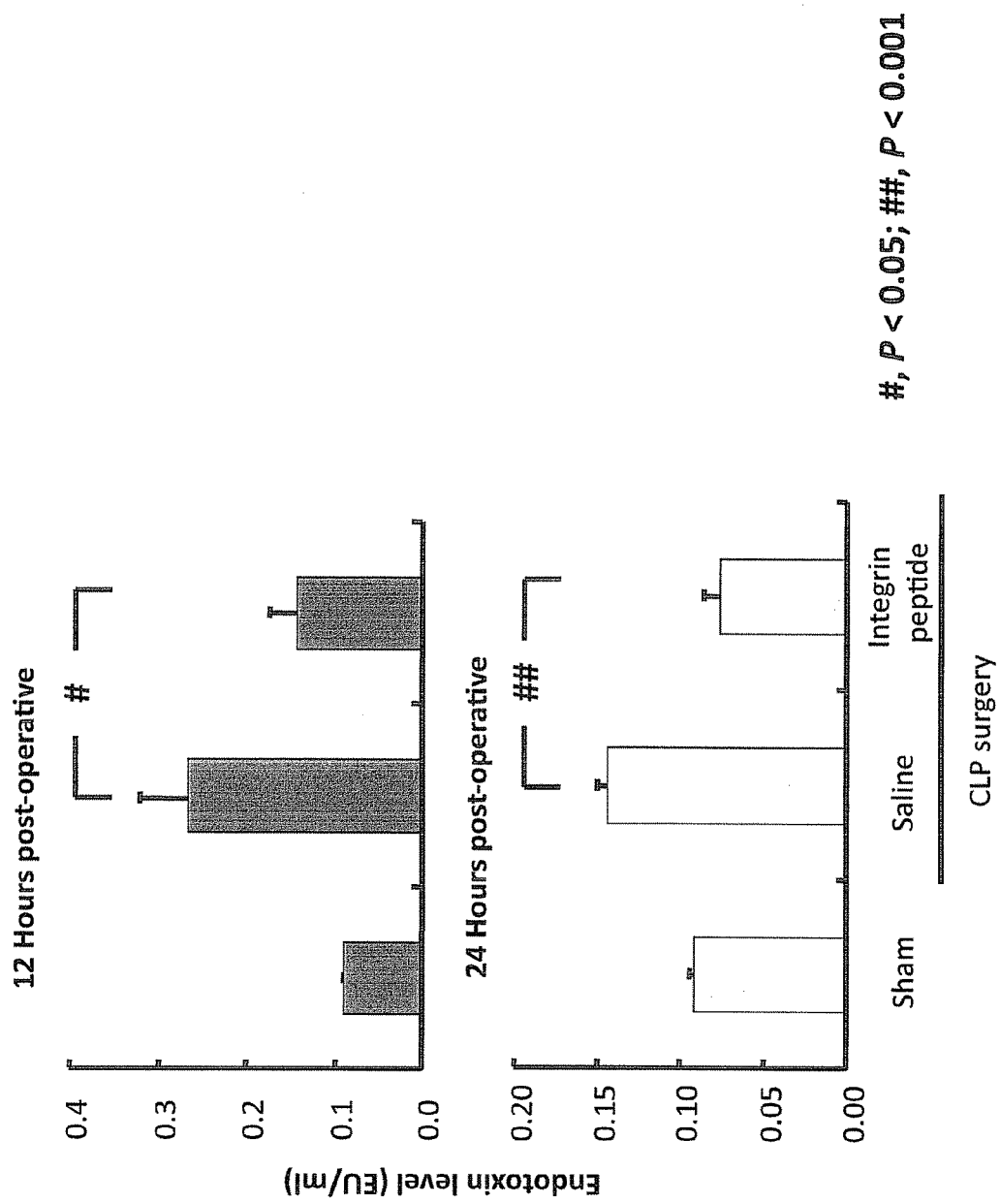
FIG. 4 is a graphic presentation of the result of serological analysis for the effect of Integrin Peptide on the biological activity of endotoxin in circulation using limulus amoebocyte lysate (LAL) chromogenic assay.

Contamination of the peritoneal cavity with intestinal bacteria led to a rapid increase in circulating endotoxin level (0.266±0.106 EU/ml) at 12 hours post-operatively, reflecting the systemic dissemination of infection (FIG. 4). The serum endotoxin levels in mice which were treated with saline remained elevated over the 24-hour post-operative period (0.143±0.006 EU/ml). In those mice which were treated with an intraperitoneal injection of Integrin Peptide, serum endotoxin levels were significantly lower than those measured in the saline-treated mice: 0.143±0.03 EU/ml vs 0.266±0.106 EU/ml at 12 hours post-operative (P<0.05); 0.076±0.001 EU/ml vs 0.143±0.006 EU/ml at 24 hours post-operative (P<0.001). These results provided unequivocal evidence that treatment with Integrin Peptide can lower circulating endotoxin levels in a patient, as exemplified by CLP-inflicted mice.

Example 4

Figure 5A:
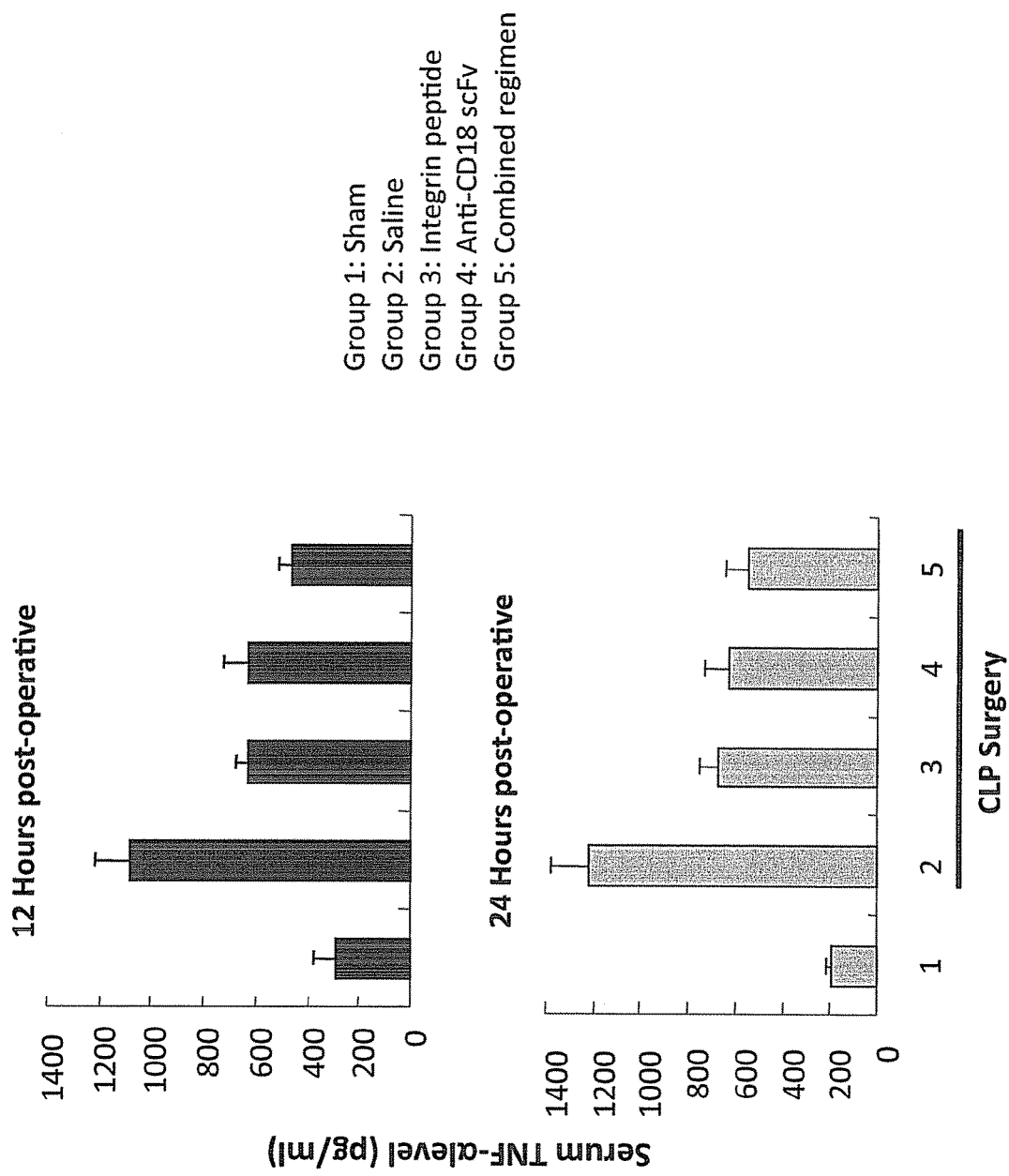
FIG. 5 is a graphic presentation of the serological analysis for the effect of Integrin Peptide, anti-CD18 βA scFv, and combined regimen on the serum level of (A) TNF-α, and (B) IL-6 of the CLP-inflicted mice.
Figure 5B:
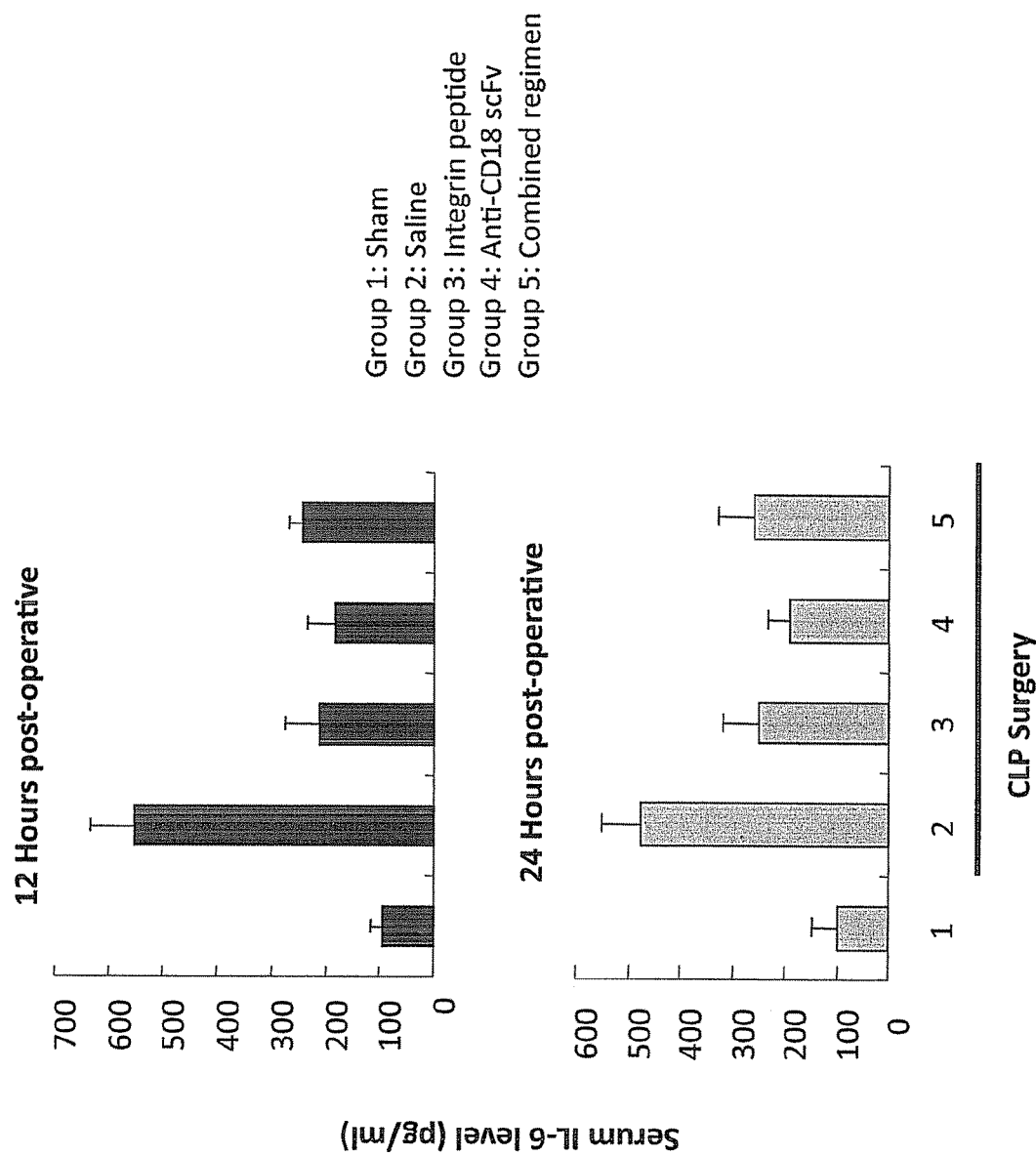

The changes in serum TNF-α and IL-6 levels in the CLP-inflicted mice after treatment with Integrin Peptide, anti-CD18 βA scFv, and in combination were measured by ELISA and the results are illustrated in FIG. 5.

At 12 hours post-operative, the serum TNF-α level of the saline-treated CLP-inflicted mice was about 1081±132 pg/ml, a value that was nearly five times greater than that of sham-operated control mice (289±90 pg/ml). Treatments of the CLP-inflicted mice with either of the therapeutic agents alone or in combination resulted in an almost 50% decrease in serum TNF-α level (PSP12, 529±43 pg/ml; Integrin Peptide, 627±98 pg/ml; anti-CD18 βA scFv, 624±50 pg/ml; and Combined regimen, 462±43 pg/ml). Serum IL-6 levels of the CLP-inflicted mice were also reduced at 12 hours post-operative after treatment with either of the therapeutic agents alone or in combination (sham-operated control, 95±19 pg/ml; saline, 550±83 pg/ml; PSP12, 256±60 pg/ml; Integrin Peptide, 212±49 pg/ml; anti-CD18 βA scFv, 182±24 pg/ml; and combined regimen, 242±38 pg/ml).

The serum levels of both cytokines in saline-treated CLP mice remained elevated 24 hours post-operative and was nearly six times higher than that of the sham-operated control mice. The responses to the various treatments of the CLP mice at 24 hours post-operative were similar to those observed in CLP mice at 12 hours post-operative: serum levels of TNF-α and IL-6 fell by 50% compared to those of the saline-treated mice.

Example 5

The modulating effect of Integrin Peptide and anti-CD18 βA scFv on infiltration of leukocytes into lung and livers of the CLP-inflicted mice was studied by measuring the CD3 mRNA content in both tissues. CD3 is a marker of inflammatory lymphocyte. To this end, immediately after sacrifice of mice lung and liver were quick frozen in liquid nitrogen. Total RNA was first extracted and purified from lung and liver, and was then used for first-strand cDNA synthesis. Amplification of CD3 from first-strand cDNA, and real-time measurement of amplified CD3 were then carried out in ABI PRISM 7700 sequence detector system (Applied Biosystems Inc., Forest Hill, Calif., USA).

The level of CD3 in lung and liver of the CLP-inflicted mice was illustrated in FIG. 6. Results showed that at 12 and 24 hours after CLP the CD3 mRNA content in both lung and liver was elevated, suggesting severe infiltration of inflammatory leukocytes into these organs. Treatment of the CLP-inflicted mice with Integrin Peptide, anti-CD18 βA scFv, and combined regimen reduced CD3 mRNA content in lung and liver. These suggested both Integrin Peptide and anti-CD18 βA scFv are able to abrogate infiltration of inflammatory leukocytes into major organs of patients.

Example 6

Figure 7:
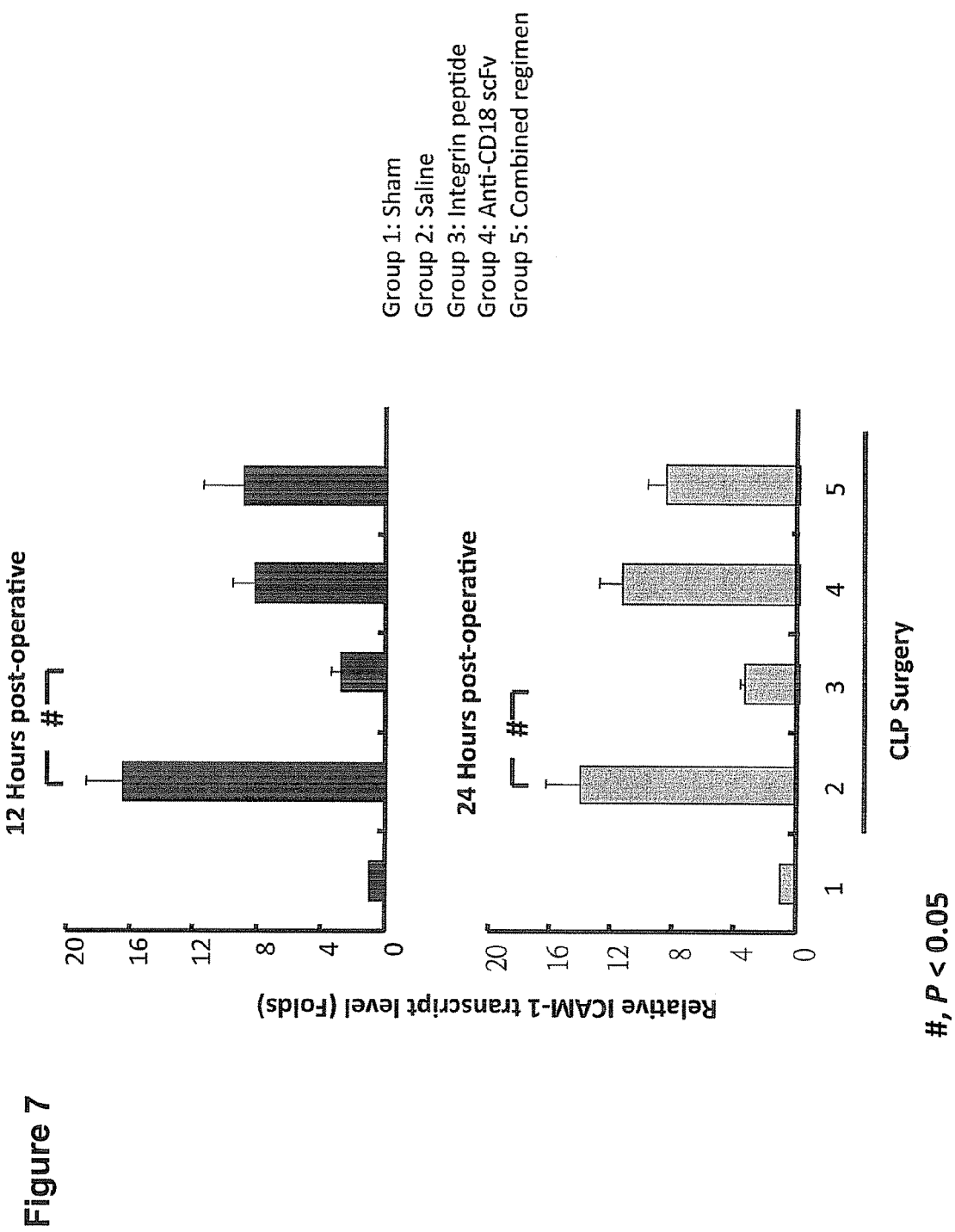
FIG. 7 is a graphic presentation of the result of expression analysis for the effect of Integrin Peptide, anti-CD18 βA scFv, and combined regimen on the intercellular adhesion molecule (ICAM)-1 expression in livers of the CLP-inflicted mice.

Real-time PCR measured the transcript level of ICAM-1 in the livers of mice that were administrated different treatments. The ICAM-1 transcript was amplified in the Power SYBR Green PCR Master Mix (Applied Biosystems) using ABI PRISM 7700 sequence detector system (Applied Biosystems). Results were calculated, and compared, and expressed as fold changes in FIG. 7.

Acute peritonitis led to significant up-regulation of ICAM-1 transcript, as reflected by the saline-treated CLP-inflicted mice of which the ICAM-1 transcripts were 14-16 times higher than those of the sham-operated control mice. The CLP-inflicted mice that received different treatments in general showed a lower ICAM-1 transcript. In particular, treatment with Integrin Peptide resulted in significant decreases in ICAM-1 transcript level when compared with those of the saline-treated mice ($P<0.05$) at both time points post-operative. Anti-CD18 βA scFv, either alone or in combination, also suppressed the CLP-induced ICAM-1 transcription. However, the modulating effect of anti-CD18 βA scFv was found to be less than that of Integrin Peptide. Thus it has been shown that the therapeutic agents of the subject invention are effective either individually or in combined regimen for down-modulating the peritonitis induced expression of ICAM-1 in livers of patients.

Figure 8:
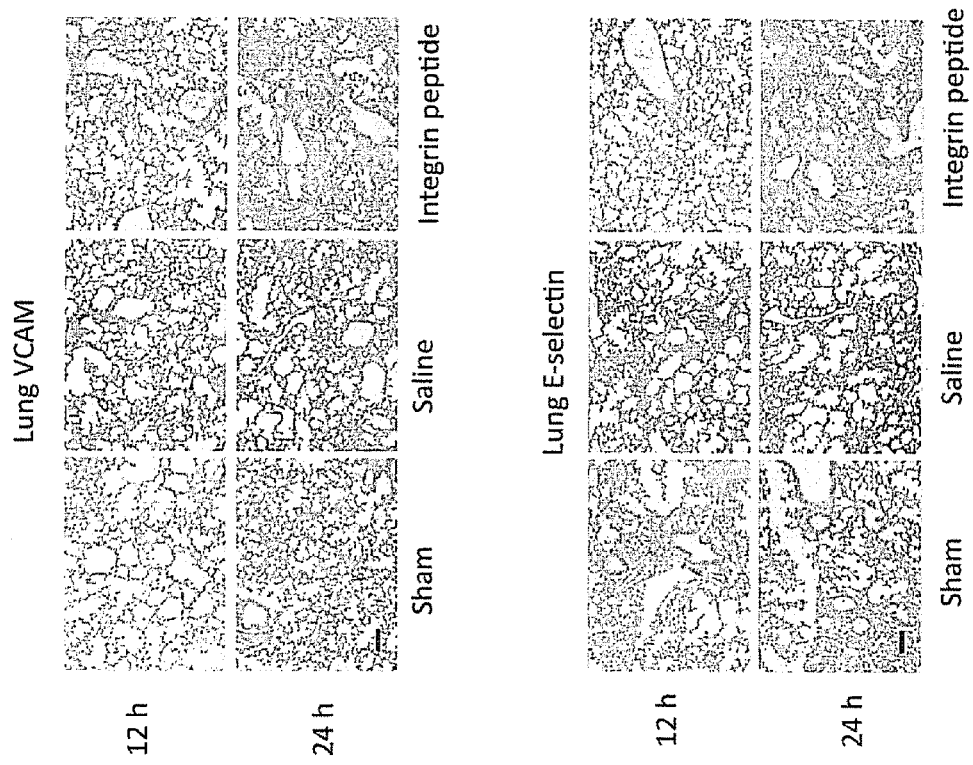
FIG. 8 is a graphic presentation of the result of immunohistochemical analysis for the effect of Integrin Peptide on the VCAM and E-selectin expression in lungs of the CLP-inflicted mice.

The modulating effect of Integrin Peptide on VCAM and E-selectin expression in lung was studied by immunohistochemistry (FIG. 8). VCAM and E-selectin are two adhesion molecules in addition to ICAM-1 on endothelium that promote leukocyte infiltration into tissues. Results showed that CLP surgery induced expression of VCAM and E-selectin in lung. Administering Integrin Peptide to CLP-inflicted mice suppressed these adhesion molecule expressions in lung, as have revealed by the reduced reactivity toward VCAM and E-selectin in lung sections.

Example 7

In addition to the cecal ligation and puncture (CLP) model, the therapeutic efficacy of Integrin Peptide has been validated in a rat model of necrotizing enterocolitis. In this model, distending the rat jejunum with bacterial LPS induces lethal systemic inflammatory response, which is as revealed by the surge in circulating TNF-α and IL-6 levels, and up-regulated expression of the TLR4 immunity components mRNA. These components include TLR4, MD-2, and CD14.

Figure 9:
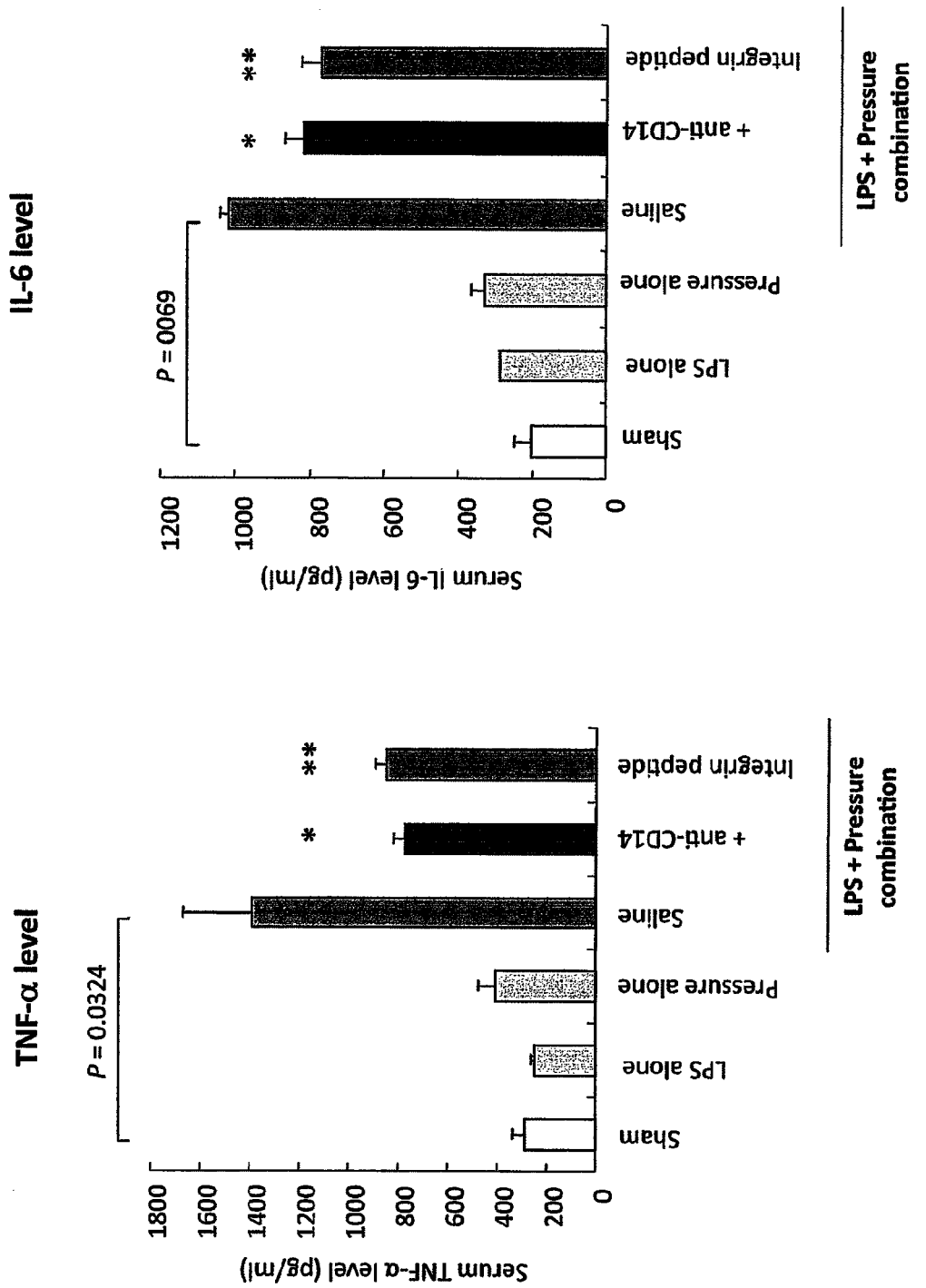
FIG. 9 is a graphic presentation of the serological analysis for the effect of Integrin Peptide on the serum level of (A) TNF-α, and (B) IL-6 of the rats of necrotizing enterocolitis model.

The circulating level of TNF-α and IL-6 was studied by cytokine ELISA (FIG. 9). As shown, distending the rat jejunum with bacterial endotoxin elevated circulating level of both TNF-α and IL-6 in a very significant manner (red bars). To test whether Integrin Peptide could reduce such cytokine level in circulation, 0.8 mg/kg Integrin Peptide was infused directly into rat jejunum. Assay on the collected blood samples showed that administered Integrin Peptide (blue bars) could reduce the circulating level of both TNF-α ($P=0.0259$) and IL-6 ($P=0.0477$), implying that Integrin Peptide is able to ameliorate bacterial LPS-induced inflammatory response.

Figure 10:
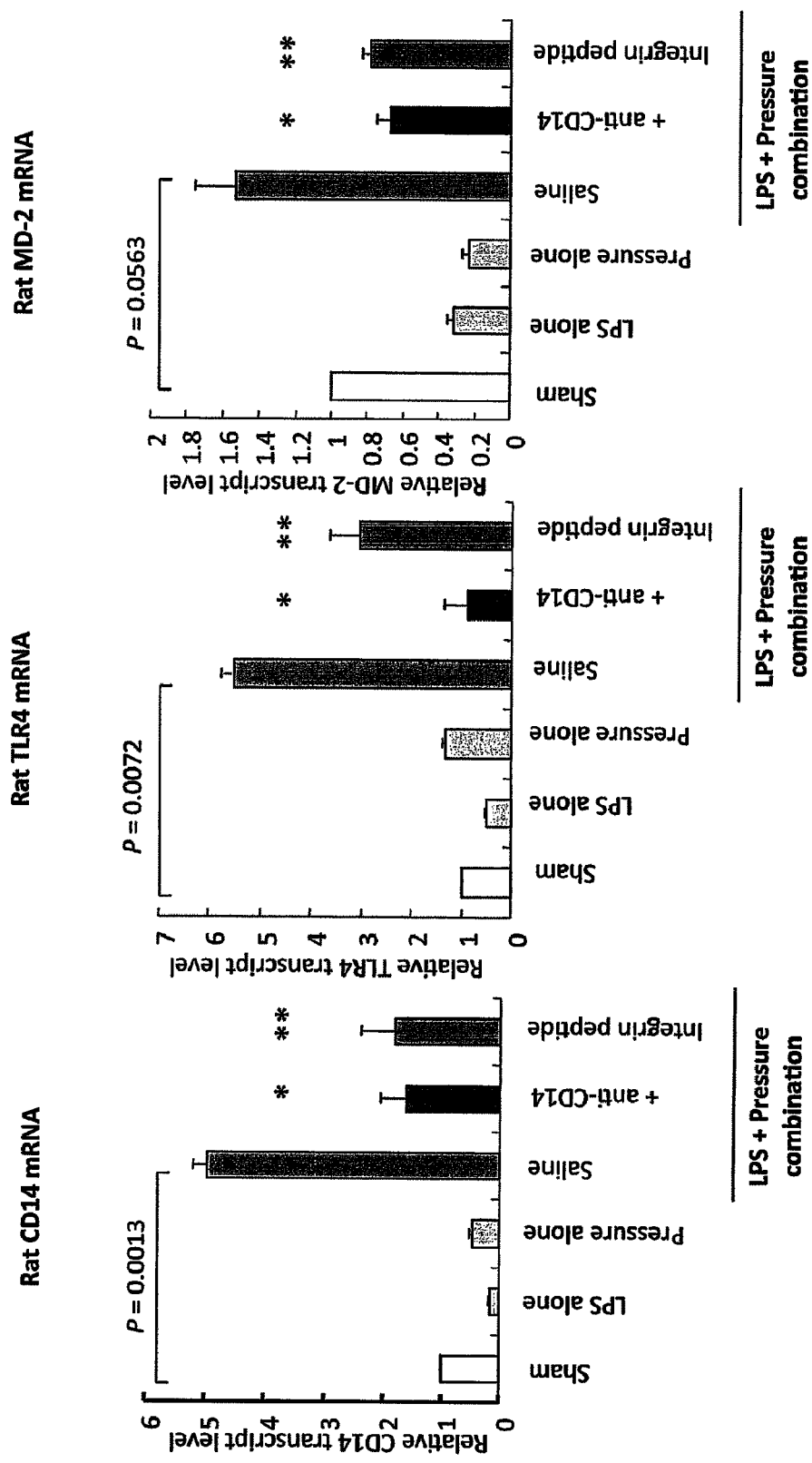
FIG. 10 is a graphic presentation of the real-time PCR analysis for the effect of Integrin Peptide on the mRNA expression of CD14, TLR4, and MD-2 of the rats of necrotizing enterocolitis.

Endotoxin-mediated inflammatory response also elevates mRNA of the innate immunity components (TLR4, MD-2, and CD 14), which were determined by real-time PCR as discussed above (FIG. 10). Distending jejunum with bacterial endotoxin provoked expression of TLR4, MD-2, and CD14 mRNA as has revealed (red bars). Infusion of Integrin Peptide suppressed these endotoxin-mediated expressions (blue bars) in significant manner: TLR4 ($P=0.00127$); MD-2 ($P=0.0187$); and CD14 ($P=0.00498$).

One of the fundamental problems in the development of novel therapies is the identification of pharmaceutical targets and the production of pharmaceutical agents against those targets. The present disclosure teaches molecular targets for use in the therapy of sepsis.

Conservative variants of the therapeutic agents of the subject invention include the exchange of an amino acid for another of like charge, size, or hydrophilicity, for example. Conservative variants of the invention may be alterations of the specified sequence such that a functionally equivalent amino acid is substituted for one or more amino acids in the peptide sequence, thus producing a silent change. For example, one or more amino acid residues within the sequence can be substituted by another amino acid of a similar polarity which acts as a functional equivalent. Substitutes for an amino acid within the sequence may be selected from other members of the class to which the amino acid belongs. For example, the non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic and glutamic acid.

A "variant" polypeptide or antibody refers herein to a molecule which differs in amino acid sequence from a "parent" polypeptide or antibody amino acid sequence by virtue of addition, deletion and/or substitution of one or more amino acid residue(s) in the parent sequence. In a preferred embodiment, the variant antibody comprises one or more amino acid substitution(s) in one or more hypervariable region(s) of the parent antibody. For example, the variant may comprise at least one, e.g. from about one to about ten, and preferably from about two to about five, substitutions in one or more hypervariable regions of the parent antibody. Ordinarily, the variant will have an amino acid sequence having at least 75% amino acid sequence identity with the parent antibody heavy or light chain variable domain sequences, more preferably at least 80%, more preferably at least 85%, more preferably at least 90%, and most preferably at least 95%. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind the receptor and preferably has properties which are superior to those of the parent antibody.

It is possible to evaluate, without undue experimentation, an antibody to determine whether it has the same specificity as anti-CD18 βA scFv of the invention by determining whether the antibody being tested prevents anti-CD18 βA scFv from binding to a particular antigen, for example the CD18 βA receptor with which anti-CD18 βA scFv is normally reactive. If the antibody being tested competes with anti-CD18 βA scFv, as shown by a decrease in binding by anti-CD18 βA scFv, then it is likely that the two antibodies bind to the same epitope.

Still another way to determine whether an antibody has the specificity of anti-CD18 βA scFv is to pre-incubate anti-CD18 βA scFv with an antigen with which it is normally reactive (for example, CD18 βA receptor), and determine if the antibody being tested is inhibited in its ability to bind the antigen. If the antibody being tested is inhibited then, in all likelihood, it has the same epitopic specificity as the anti-CD18 βA scFv of the invention.

Example 8

Screening Assay

The ability of candidate compounds to bind to CD18 βA is assessed by a competitive binding assay. Candidate compounds can be peptide or non-peptide compounds. Binding to CD18 BA is quantified by the ability to displace anti-CD18 βA or a conservative variant thereof, from CD18 βA. Displaced anti-CD18 βA or a conservative variant thereof, can be assayed by a number of techniques. For example, radiolabeled peptide can be synthesized using commercially available radiolabeled amino acids precursors. Peptides radiolabeled with $^{3}H$, $^{14}C$ or $^{35}S$ can be quantified by routine liquid scintillation techniques. Alternatively, a fluorescent labeled peptide can be synthesized. For example, lysine can be inserted in a non-critical position and labeled with fluroescein isothiocyanate ("FITC"). In addition to FITC, the peptide may be labeled with any suitable flurophore. Separation of bound from unbound peptide and quantitation of displaced peptide can be performed by routine techniques known to one of skill in the art. This embodiment of the invention is not limited by the method used to quantify the displaced peptide, and any suitable analytical technique may be used and be within the scope of the invention.

Example 9

In order to obtain more effective inhibitory peptides, standard techniques of designing derivative structures can be used to produce candidates to be tested for enhanced inhibitory capacity.

For example, one derivative peptide strategy is to subject the consensus sequence peptide to an alanine-screening procedure as described by Cunningham and Wells, 1989. Alanine can be separately introduced into each position to identify specific side chains in the peptide that modulate binding to CD18 βA. Once identified, such amino acids are exchanged for conservative amino acid substitutions. Such substitutions are of amino acids of like charge, e.g., as described by Dayoff et al., Atlas of Protein Sequence and Structure; vol 5, Suppl. 3, pp 3,45-362 (M. O. Dayoff, ed., Nat'l BioMed Research Fdn., Washington, D.C. 1979). An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as conservative variants. This type of derivative strategy has also been successful at identifying higher affinity peptides (Ohman et al., 1995; Adgey, 1998). In addition to binding to CD18 βA (via, for example, the screening assay of EXAMPLE 7 above), conservative variants can also be screened for other desirable properties such as a longer serum-half life or desirable other pharmacokinetic or pharmacodynamic properties.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

---

What is claimed is:

1. A method for treating a mammal having an endotoxin-mediated inflammatory response, comprising:
   administering to a mammal a therapeutic composition comprising:
   an Integrin peptide consisting of SEQ ID NO. 1;
   wherein the mammal is suffering from an endotoxin-mediated pro-inflammatory response.

2. The method of claim 1, wherein the endotoxin-mediated pro-inflammatory response is acute sepsis.

3. The method of claim 1, wherein the endotoxin-mediated pro-inflammatory response is caused by the presence of bacterial lipopolysaccharide.

4. The method of claim 1, wherein the mammal is a human.

5. The method of claim 1, wherein the dosage of the Integrin peptide is from about 0.01 mg to about 100 mg per kg body weight of the mammal.

6. The method of claim 1, wherein the dosage of the Integrin peptide is from about 0.1 mg to about 20 mg per kg body weight of the mammal.

7. The method of claim 1, wherein the Integrin peptide is from about 0.5 mg to about 5 mg per kg body weight of the mammal.

8. The method of claim 1, the therapeutic composition further comprising a single-chain polypeptide consisting of SEQ ID NO. 3.

9. The method of claim 1, wherein the Integrin peptide consists of 53 amino acid residues.

10. The method of claim 1, wherein administering the therapeutic composition reduces the release of pro-inflammatory cytokines.

11. The method of claim 1, wherein the therapeutic composition further comprises a pharmaceutically acceptable carrier.

12. The method of claim 1, wherein the Integrin peptide binds with lipopolysaccharide derived from gram-negative bacterial in the plasma of the mammal.

* * * * *

SEQUENCE LISTING

```
<160> NUMBER OF SEQ ID NOS: 12

<210> SEQ ID NO 1
<211> LENGTH: 53
<212> TYPE: PRT
<213> ORGANISM: Homo sapiens

<400> SEQUENCE: 1

Leu Glu Asp Asn Leu Tyr Arg Ser Asn Glu Phe Asp Tyr Pro Ser Val
1               5                   10                  15

Gly Gln Leu Ala His Lys Leu Ala Glu Asn Asn Ile Gln Pro Ile Phe
            20                  25                  30

Ala Val Thr Ser Arg Met Val Lys Thr Tyr Glu Lys Leu Thr Glu Ile
        35                  40                  45

Ile Pro Lys Ser Ala
    50
```

<210> SEQ ID NO 2
<211> LENGTH: 252
<212> TYPE: DNA
<213> ORGANISM: Homo sapiens

<400> SEQUENCE: 2 accccaacg acggccgctg tcacctggag gacaacttgt acaagaggag caacgaattc    60
gactacccat cggtgggcca gctggcgcac aagctggctg aaaacaacat ccagcccatc   120
ttcgcggtga ccagtaggat ggtgaagacc tacgagaaac tcaccgagat catccccaag   180
tcagccgtgg gggagctgtc tgaggactcc agcaatgtgg tccatctcat taagaatgct   240
tacaataaac tc                                                       252

<210> SEQ ID NO 3
<211> LENGTH: 234
<212> TYPE: PRT
<213> ORGANISM: Artificial Sequence
<220> FEATURE:
<223> OTHER INFORMATION: Anti-CD18 scFv antibody

<400> SEQUENCE: 3

Val Lys Leu Gln Gln Ser Gly Thr Glu Val Val Lys Pro Gly Ala Ser
1               5                   10                  15

Val Lys Leu Ser Cys Lys Ala Ser Gly Tyr Ile Phe Thr Ser Tyr Asp
            20                  25                  30

Ile Asp Trp Val Arg Gln Thr Pro Glu Gln Gly Leu Glu Trp Ile Gly
        35                  40                  45

Trp Ile Phe Pro Gly Glu Gly Ser Thr Glu Tyr Asn Glu Lys Phe Lys
    50                  55                  60

Gly Arg Ala Thr Leu Ser Val Asp Lys Ser Ser Ser Thr Ala Tyr Met
65                  70                  75                  80

Glu Leu Thr Arg Leu Thr Ser Glu Asp Ser Ala Val Tyr Phe Cys Ala
                85                  90                  95

Arg Gly Asp Tyr Thr Tyr Arg Arg Tyr Phe Asp Leu Trp Gly Gln Gly
            100                 105                 110

Thr Thr Val Thr Val Ser Ser Cys Gly Gly Ser Gly Gly Gly Gly
        115                 120                 125

Ser Gly Gly Gly Gly Ser Ser Asp Ile Glu Leu Thr Gln Ser Pro Ala
130                 135                 140

Ile Met Ser Ala Ser Pro Gly Glu Arg Val Thr Met Thr Cys Ser Ala
145                 150                 155                 160

Ser Ser Ser Ile Arg Tyr Ile Tyr Trp Tyr Gln Gln Lys Pro Gly Ser
                165                 170                 175

Ser Pro Arg Leu Leu Ile Tyr Asp Thr Ser Asn Val Ala Pro Gly Val
            180                 185                 190

Pro Phe Arg Phe Ser Gly Ser Gly Ser Gly Thr Ser Tyr Ser Leu Thr
        195                 200                 205

Ile Asn Arg Met Glu Ala Glu Asp Ala Ala Thr Tyr Tyr Cys Gln Glu
    210                 215                 220

Trp Ser Gly Tyr Pro Tyr Thr Phe Gly Gly
225                 230

<210> SEQ ID NO 4
<211> LENGTH: 738
<212> TYPE: DNA
<213> ORGANISM: Artificial Sequence
<220> FEATURE:
<223> OTHER INFORMATION: Anti-CD18 scFv antibody cDNA -continued

<400> SEQUENCE: 4

```
gtgaagctgc agcagtcagg aactgaagtg gtaaagcctg gggcttcagt gaagttgtcc    60
tgcaaggctt ctggctacat cttcacaagt tatgatatag actgggtgag cagacgcct   120
gaacagggac ttgagtggat tggatggatt tttcctggag aggggagtac tgaatacaat   180
gagaagttca agggcagggc cacactgagt gtagacaagt cctccagcac agcctatatg   240
gagctcacta ggctgacatc tgaggactct gctgtctatt tctgtgctag aggggactac   300
tataggcgct actttgactt gtggggccaa gggaccacgg tcaccgtctc ctcatgtgga   360
ggcggttcag gcggaggtgg ctctggcggt ggcggatctg acattgagct cacccagtct   420
ccagcaatca tgtctgcatc tccaggggag agggtcacca tgacctgcag tgccagctca   480
agtatacgtt acatatattg gtaccaacag aagcctggat cctcccccag actcctgatt   540
tatgacacat ccaacgtggc tcctggagtc ccttttcgct tcagtggcag tgggtctggg   600
acctcttatt ctctcacaat caaccgaatg gaggctgagg atgctgccac ttattactgc   660
caggagtgga gtggttatcc gtacacgttc ggaggggggtg cgccggtgcc gtatccggat   720
ccgctggaac cgagtgcc                                                 738
```

<210> SEQ ID NO 5
<211> LENGTH: 120
<212> TYPE: PRT
<213> ORGANISM: Homo sapiens

<400> SEQUENCE: 5

```
Val Lys Leu Gln Gln Ser Gly Thr Glu Val Val Lys Pro Gly Ala Ser
 1               5                  10                  15
Val Lys Leu Ser Cys Lys Ala Ser Gly Tyr Ile Phe Thr Ser Tyr Asp
                20                  25                  30
Ile Asp Trp Val Arg Gln Thr Pro Glu Gln Gly Leu Glu Trp Ile Gly
        35                  40                  45
Trp Ile Phe Pro Gly Glu Gly Ser Thr Glu Tyr Asn Glu Lys Phe Lys
    50                  55                  60
Gly Arg Ala Thr Leu Ser Val Asp Lys Ser Ser Ser Thr Ala Tyr Met
65                  70                  75                  80
Glu Leu Thr Arg Leu Thr Ser Glu Asp Ser Ala Val Tyr Phe Cys Ala
                85                  90                  95
Arg Gly Asp Tyr Tyr Arg Arg Tyr Phe Asp Leu Trp Gly Gln Gly
                100                 105                 110
Thr Thr Val Thr Val Ser Ser Cys
            115                 120
```

<210> SEQ ID NO 6
<211> LENGTH: 100
<212> TYPE: PRT
<213> ORGANISM: Homo sapiens

<400> SEQUENCE: 6

```
Ser Asp Ile Glu Leu Thr Gln Ser Pro Ala Ile Met Ser Ala Ser Pro
 1               5                  10                  15
Gly Glu Arg Val Thr Met Thr Cys Ser Ala Ser Ser Ser Ile Arg Tyr
                20                  25                  30
Ile Tyr Trp Tyr Gln Gln Lys Pro Gly Ser Ser Pro Arg Leu Leu Ile
        35                  40                  45
Tyr Asp Thr Ser Asn Val Ala Pro Gly Val Pro Phe Arg Phe Ser Gly
    50                  55                  60
```

-continued

Ser Gly Ser Gly Thr Ser Tyr Ser Leu Thr Ile Asn Arg Met Glu Ala
65                  70                  75                  80

Glu Asp Ala Ala Thr Tyr Tyr Cys Gln Glu Trp Ser Gly Tyr Pro Tyr
                85                  90                  95

Thr Phe Gly Gly
            100

<210> SEQ ID NO 7
<211> LENGTH: 17
<212> TYPE: PRT
<213> ORGANISM: Homo sapiens

<400> SEQUENCE: 7

Trp Ile Phe Pro Gly Glu Gly Ser Thr Glu Tyr Asn Glu Lys Phe Lys
1               5                   10                  15

Gly

<210> SEQ ID NO 8
<211> LENGTH: 11
<212> TYPE: PRT
<213> ORGANISM: Homo sapiens

<400> SEQUENCE: 8

Gly Asp Tyr Thr Tyr Arg Arg Tyr Phe Asp Leu
1               5                   10

<210> SEQ ID NO 9
<211> LENGTH: 10
<212> TYPE: PRT
<213> ORGANISM: Homo sapiens

<400> SEQUENCE: 9

Ser Ala Ser Ser Ser Ile Arg Tyr Ile Tyr
1               5                   10

<210> SEQ ID NO 10
<211> LENGTH: 7
<212> TYPE: PRT
<213> ORGANISM: Homo sapiens

<400> SEQUENCE: 10

Asp Thr Ser Asn Val Ala Pro
1               5

<210> SEQ ID NO 11
<211> LENGTH: 9
<212> TYPE: PRT
<213> ORGANISM: Homo sapiens

<400> SEQUENCE: 11

Gln Glu Trp Ser Gly Tyr Pro Tyr Thr
1               5

<210> SEQ ID NO 12
<211> LENGTH: 5
<212> TYPE: PRT
<213> ORGANISM: Homo sapiens

<400> SEQUENCE: 12

Ser Tyr Asp Ile Asp
1               5